(12) United States Patent
Osborn, III et al.

(10) Patent No.: US 7,213,466 B2
(45) Date of Patent: May 8, 2007

(54) TAMPON-AND-APPLICATOR SYSTEMS AND METHOD FOR IN VITRO TESTING THEREOF

(75) Inventors: Thomas Ward Osborn, III, Clifton, OH (US); Diana Lynne Gann, Lebanon, OH (US); Jeanne Marie Hughes, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 196 days.

(21) Appl. No.: 10/861,711

(22) Filed: Jun. 4, 2004

(65) Prior Publication Data

US 2005/0273036 A1 Dec. 8, 2005

(51) Int. Cl.
*G01N 3/08* (2006.01)
(52) U.S. Cl. ..................................... 73/824
(58) Field of Classification Search ........... 73/824, 73/800, 818
See application file for complete search history.

(56) References Cited

U.S. PATENT DOCUMENTS

| 3,760,808 | A | 9/1973 | Bleuer |
| 3,850,160 | A * | 11/1974 | Denson ................. 600/572 |
| 4,479,791 | A | 10/1984 | Sprague |
| 4,726,805 | A | 2/1988 | Sanders, III |
| 4,846,802 | A | 7/1989 | Sanders, III |
| 4,960,417 | A | 10/1990 | Tarr, Jr. |
| 5,279,541 | A | 1/1994 | Frayman |
| 5,348,534 | A | 9/1994 | Tomaszewski |
| 5,904,671 | A * | 5/1999 | Navot et al. ............ 604/361 |
| 6,524,269 | B2 * | 2/2003 | McNamara ............ 604/12 |
| 6,837,882 | B2 * | 1/2005 | Agyapong et al. ...... 604/385.17 |

* cited by examiner

*Primary Examiner*—Max Noori
(74) *Attorney, Agent, or Firm*—James E. Oehlenschlager; David M. Weirich; Ken K. Patel

(57) ABSTRACT

A method and an apparatus for in vitro testing of catamenial tampon-and-applicator systems are disclosed. The apparatus comprises an in vitro receptacle for accepting tampons deployed during the testing procedure. The in vitro receptacle comprises a sleeve with a tampon-deflecting zone, representing an in vivo vaginal channel with a frontal area of a cervix.

10 Claims, 26 Drawing Sheets

US 7,213,466 B2

TAMPON-AND-APPLICATOR SYSTEMS AND METHOD FOR IN VITRO TESTING THEREOF

FIELD OF THE INVENTION

The present invention relates to catamenial tampon-and applicator systems providing for placement of a tampon within the boundaries of a low-placement positioning zone according to a method of the present invention for in vitro testing of tampon-and-applicator systems.

BACKGROUND OF THE INVENTION

Catamenial tampon-and-applicator systems referred herein to a combination of a tampon applicator and a tampon housed in the applicator, to be self-used by a user to insert the tampon into the vagina to absorb menstrual fluid to prevent leakage of the fluid from the vagina. Commercial tampons are rated by their capacity to absorb and hold a certain amount of fluid, defined by the industry standards regulating commercial labeling of the tampons, dividing them into several categories, such as "junior," "regular," "super," and the like, by a standard Syngyna Absorbency test method FDA 21 CFR 801.430

However, some tampons, regardless of their rated capability to absorb and hold fluid, fail to prevent leakage before the tampon reaches its rated absorbent capacity, allowing the menstrual fluid to bypass the tampon along vaginal walls. This problem has been known as a premature leakage. Typically in the industry, the premature leakage problem has been addressed by improving various performance characteristics of the tampons, for example, the ability of the tampons to absorb menstrual fluid faster and to swell faster inside the vagina in order to prevent menstrual fluid from bypassing the tampon along the vaginal walls. However, despite such product improvements, which typically require considerable cost, most tampons will still fail to prevent premature leakage, i.e., before they become saturated with the rated amount of the absorbed liquid.

In this respect, it has been surprisingly discovered by the applicants that the instances of premature leakage can be substantially reduced by placing tampons into a certain "target" position inside a vagina. This target placement position is different from the positions typically achieved by the use of the currently marketed tampon-and-applicator systems.

This target placement position has been identified by the applicants as a "low placement positioning" because in this position, the tampon of the tampon-and-application system of the present invention is inserted into the vagina not as deep as the tampon inserted by the use of the current tampon-and-applicator systems. The low placement positioning of the tampon can be provided by the novel low placement applicators discovered by the applicants and disclosed in the patent applications (P&G case numbers 9660, 9661, 9662, 9663 and 9664) filed Jun. 4, 2004 coincidentally with the instant patent application and hereby incorporated by reference herein.

FIG. 1 is a coronal MRI image of a tampon user having a tampon in the vagina, inserted by the user using a typical commercial tampon-and-applicator system. In comparison, FIG. 2 is a coronal MRI image of a tampon user having a tampon in the vagina, inserted by the user using a tampon-and-applicator system of the present invention.

In FIG. 1, a tampon 10 is inserted substantially deeper in the vagina than a tampon 10A in FIG. 2. The deeper insertion of the tampon 10 results in deflecting of the leading end 11 of the tampon 10 by the cervix 18, specifically by the frontal area 19 of the cervix 18 (deflecting the leading end 11 of the tampon 10 to the left, as shown in FIG. 1, or to the right, depending on the anatomy of the user), and in having the leading end 11 of the tampon 10 being disposed substantially posterior of the frontal area 19 of the cervix 18.

In comparison to FIG. 1, FIG. 2 demonstrates the most preferred position of the tampon 10A according to the present invention, when the leading end 11 of the tampon 10A is disposed anterior of the frontal area 19 of the cervix 18. It should be noted, as will be disclosed in more detail below, that the "lower placement position" discovered by the applicants can include instances when the leading end 11 of the tampon 10A is slightly posterior of the frontal area 19 of the cervix 18.

However, with respect to applicants discovery of the low-placement positioning, the commonly used standard Syngina test method referenced above does not address the inventors' discovery. Further, the Syngina method does not address the positioning of the tampon in the vagina with respect to the cervix in particular to the frontal area of the cervix. Therefore, there is a need for a novel method for in vitro testing of tampon-and-applicator systems.

SUMMARY OF THE INVENTION

In one aspect, the present invention is directed to a method of in vitro testing of catamenial tampon-and-applicator systems. The method comprises the steps of:

(a) pressurizing an in vitro receptacle comprising a sleeve having a tampon-deflecting zone;

(b) providing a tampon-and-applicator system comprising an applicator at least partially housing a tampon in a larger tube and a smaller tube for ejecting the tampon from the larger tube, the tampon having a removal string attached thereto;

(c) inserting the tampon-and-applicator system into an adaptor such that a trailing end of a larger tube of the tampon-and-applicator system is even with a trailing end of the adaptor;

(d) inserting the adaptor with the tampon-and-applicator system into an entry of the vitro receptacle such that a leading end of the adaptor is brought in contact with a base surface in the entry;

(e) activating a driving mechanism to push the smaller tube to eject the tampon from the tampon-and-applicator system into the in vitro receptacle;

(f) removing the adaptor with the applicator from the entry of the in vitro receptacle leaving the tampon in the in vitro receptacle;

(g) inserting a pin plug into the entry of the in vitro receptacle; and (h) photographing the tampon and a low-placement positioning zone disposed inside the in vitro receptacle, the low-placement positioning zone having a width and forming an anterior depth and a posterior depth.

In another aspect, the present invention is directed to a tampon-and-applicator system comprising a tampon, an applicator at least partially housing the tampon and a withdrawal element attached thereto, wherein the tampon-and-applicator system provides for placement of the tampon within the boundaries of a low-placement positioning zone according to a method for in vitro testing of tampon-and-applicator systems.

BRIEF DESCRIPTION OF THE DRAWINGS

In the drawings, like reference numbers indicate identical or functionally similar elements.

DETAILED DESCRIPTION OF THE INVENTION

Figures 1, 2:
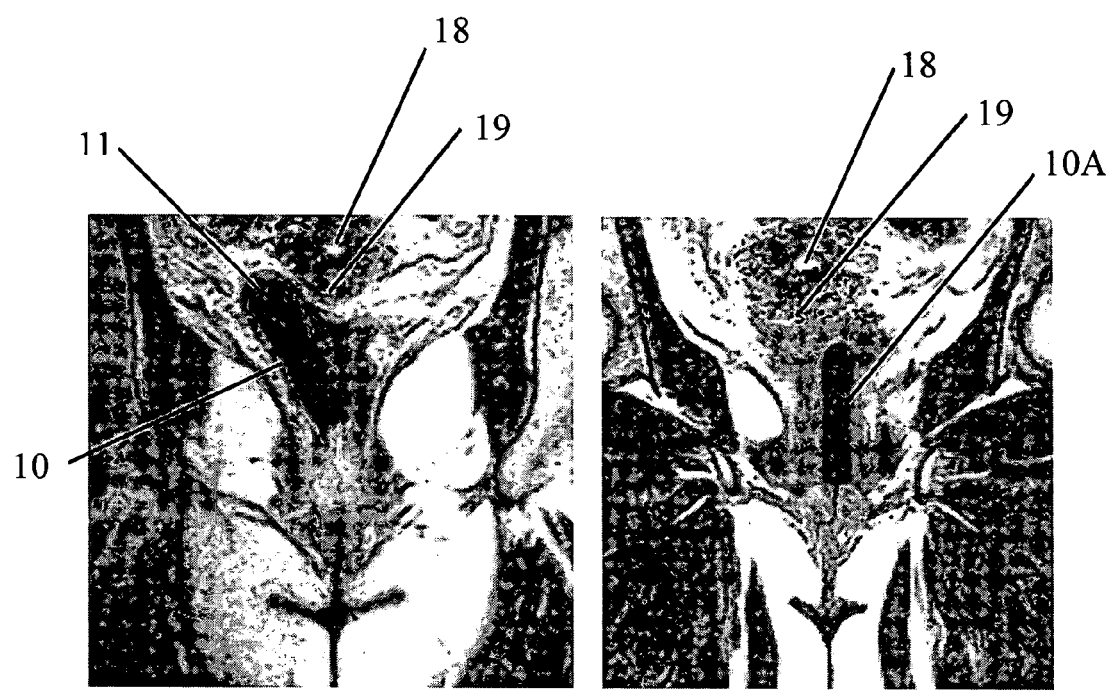
FIG. 1 is a coronal MRI image of a tampon user having a tampon in the vagina, inserted by a user using a typical commercial tampon-and-applicator system.
FIG. 2 is a coronal MRI image of a tampon user having a tampon in the vagina, inserted by a user using a tampon-and-applicator system of the present invention.

The present invention relates to personal care products and particularly to catamenial tampon-and applicator systems providing for placement of a tampon within the boundaries of a low-placement positioning zone according to the method of the present invention for in vitro testing of tampon-and-applicator systems. The method of the present invention includes a testing apparatus comprising a novel testing device, identified herein as an in vitro receptacle, simulating relevant in vivo anatomical and physical characteristics affecting the positioning of a tampon deployed by a tampon applicator of a tampon-and-applicator system activated by a user during a tampon insertion procedure.

The method and the apparatus of the present invention will be described in the terms of one exemplary embodiment that the applicants found particularly suitable; however, it should be noted that other suitable embodiments could be feasible within the scope of the present invention.

Within the scope of this specification, each term or phrase below will include the following meaning or meanings. These terms, however, may be defined further with additional language in other portions of the specification and/or the depiction in the figures.

The term "tampon-and-applicator system" refers to the combination of an applicator and a tampon housed, at least partially, inside the applicator.

The term "tampon" refers herein to any type of absorbent structure that can be inserted into a human vagina for the absorption of menses therefrom. In particular, the term "tampon" refers herein to both so called self-sustaining-shape and non-self-sustaining-shape tampons known in the industry, having a generally cylindrical configuration ranging about 30 to 60 mm in length and from 8 to 20 mm in width. However, it should be noted that the term "tampon" does not exclude herein tampons intended to aid in wound healing or to deliver active materials including medicamentous or moisture. Furthermore, this term "tampon" does not exclude herein devices intended to help control incontinence, which can comprise non-absorbent or at least partially absorbent materials.

The term "applicator" refers herein to a device as a part of a tampon-and-applicator system, used for inserting the tampon into a vagina. A typical applicator includes two telescoping tubes, wherein a larger tube contains a tampon (fully or partially enclosed, depending on the design), and a smaller tube serves as a plunger for pushing the tampon from the larger tube, and wherein after the completion of pushing action, depending on the design, the tampon is fully or partially expelled from the larger tube. The user typically inserts the applicator into the vagina according to manufacturer instructions and pushes the smaller tube to a predetermined position (for example, a position at which the trailing ends of both tubes are even and the smaller tube cannot be pushed any further, or, alternatively, when for the convenience of the user a smaller tube has a flange-like trailing end, the smaller tube cannot be pushed further when its flange-like trailing end is pushed against the trailing end of the larger tube). After the deployment, the user removes the empty applicator from the vagina, leaving the tampon in the vagina.

The term "low-placement positioning" refers herein to a position at which a tampon (inserted into a human vagina by a user of a tampon-and-applicator system containing the tampon) is placed in the vagina less posterior than the position typically resulting from using commercial tampon-and-applicator systems.

The term "low-placement positioning zone" refers herein to a horizontal area inside the apparatus of the present invention, representing an area in a coronal section of a human vagina between a hymenal ring and the frontal area of a cervix.

The term "method for in vitro testing of tampon-and-applicator systems" refers herein to the method of the present invention utilizing the in vitro receptacle of the present invention comprising a tampon-deflecting zone representing a frontal area of a cervix of a human vagina.

Figure 3:
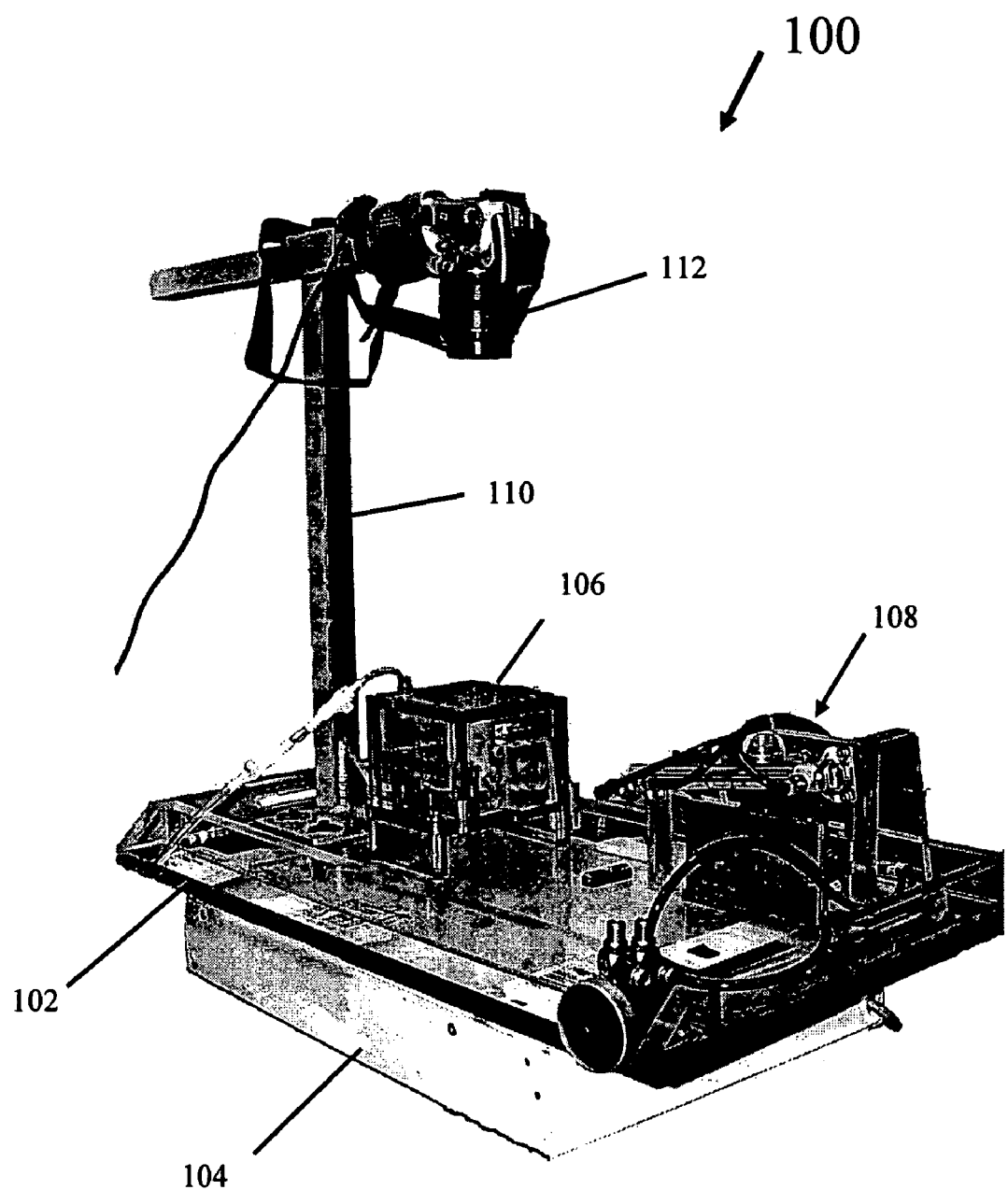
FIG. 3 is a photograph of a test stand of the present invention for in vitro testing of tampon-and-application systems by the method of the present invention.
Figure 4:
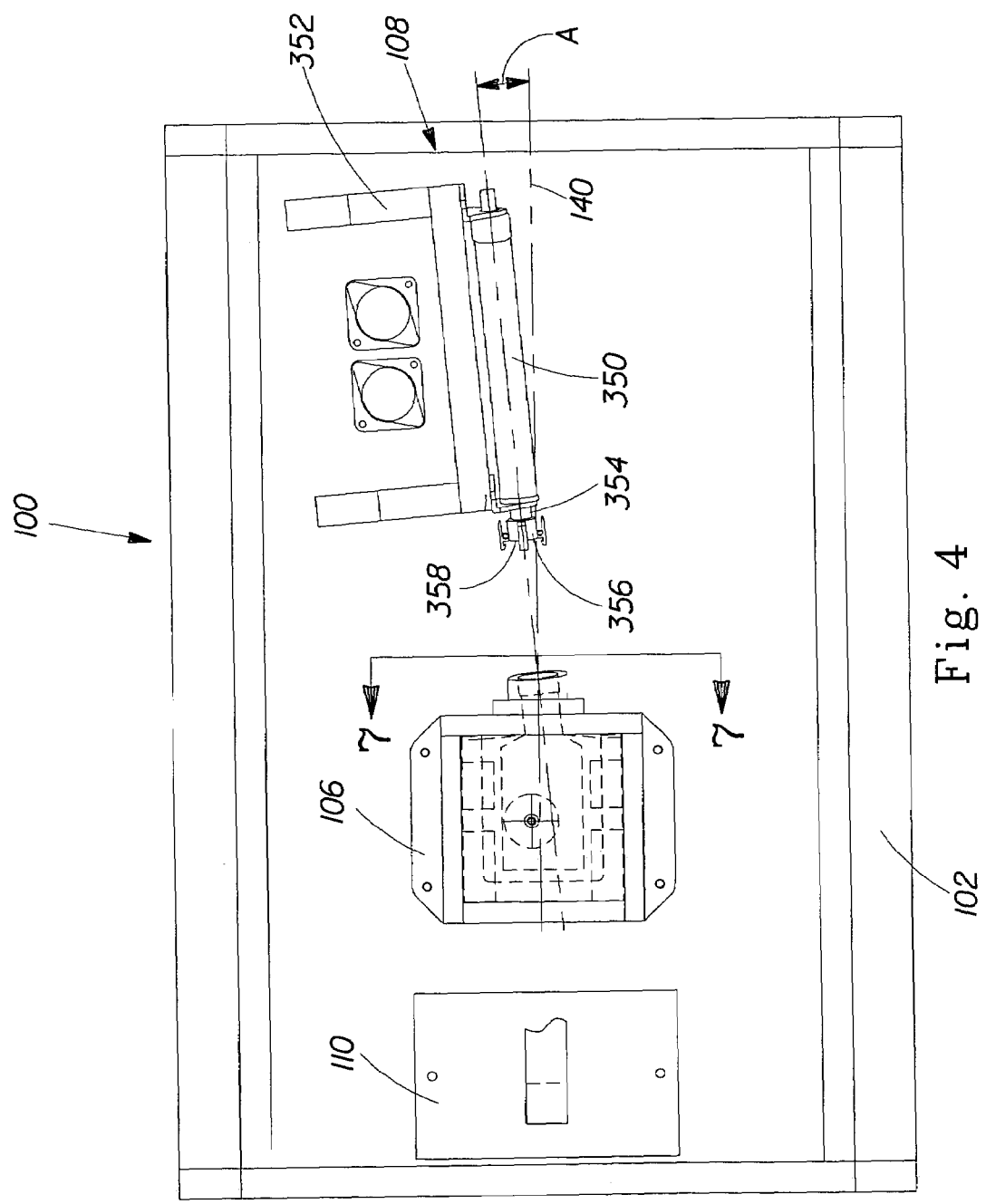
FIG. 4 is a top plan view of the test stand of FIG. 3 (not showing, for clarity, a photo camera of FIG. 3).
Figure 5:
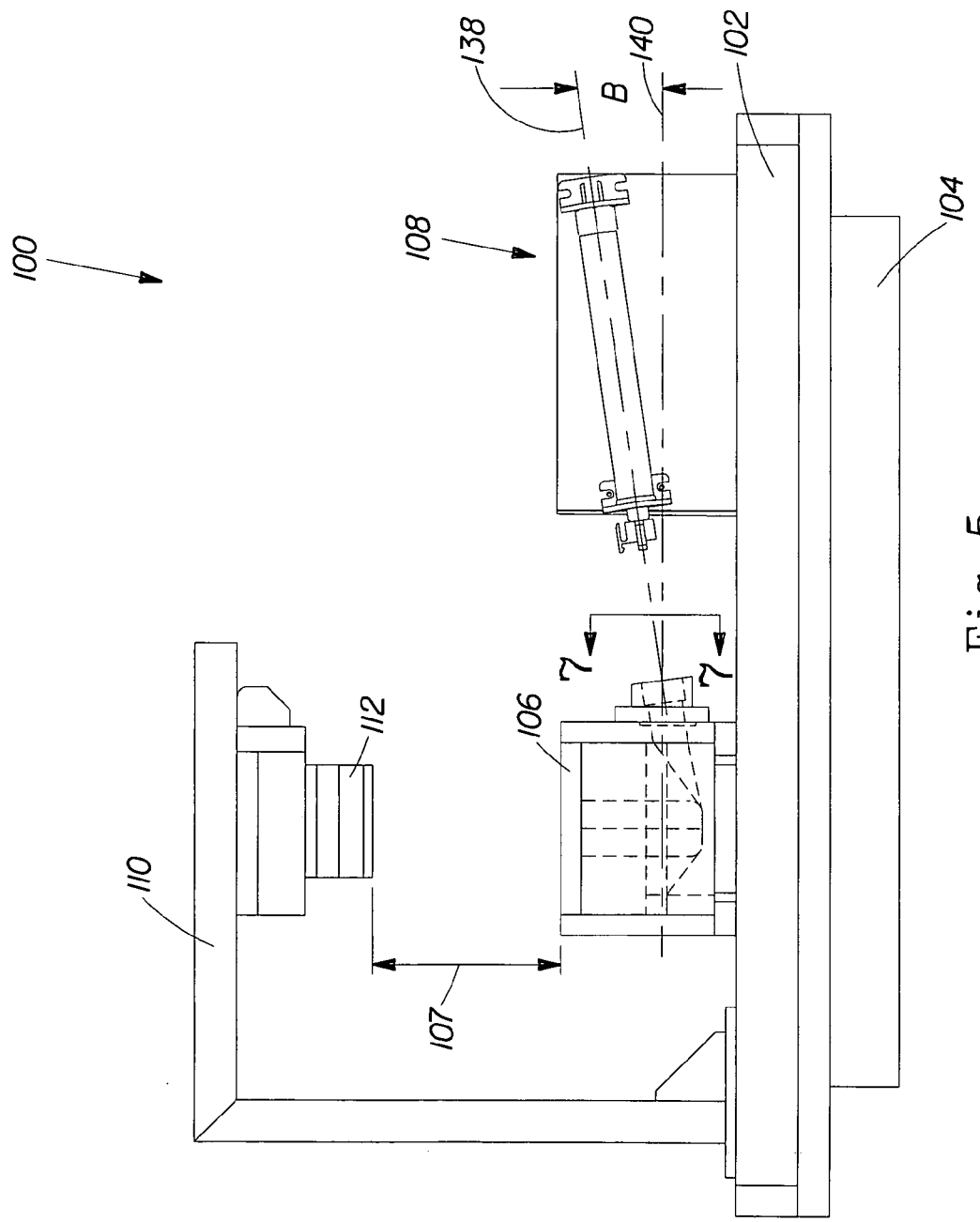
FIG. 5 is a side elevation view of the test stand of FIG. 3.
Figure 6:
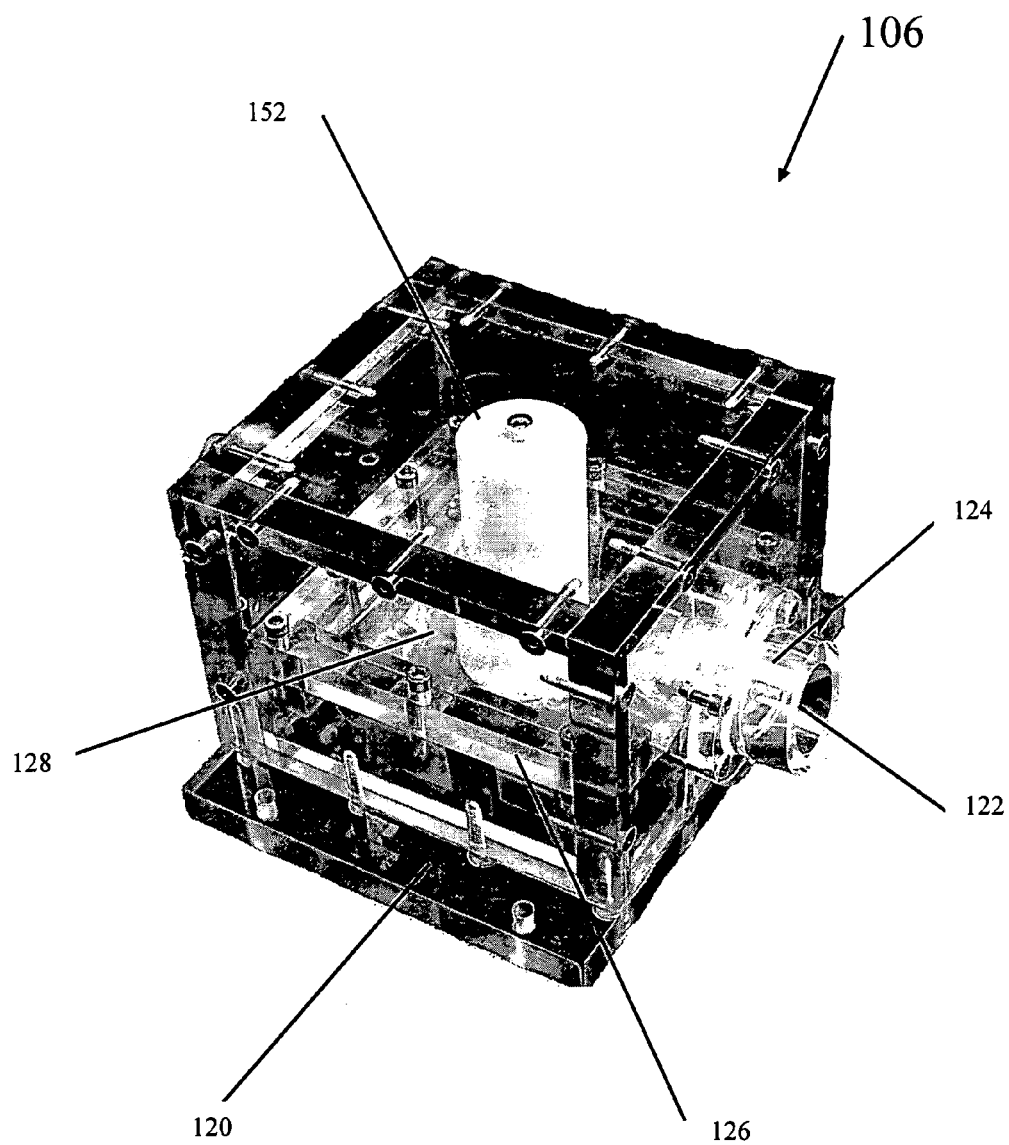
FIG. 6 is a photograph of an in vitro receptacle of the test stand of FIGS. 3–5, having transparent walls.
Figure 7:
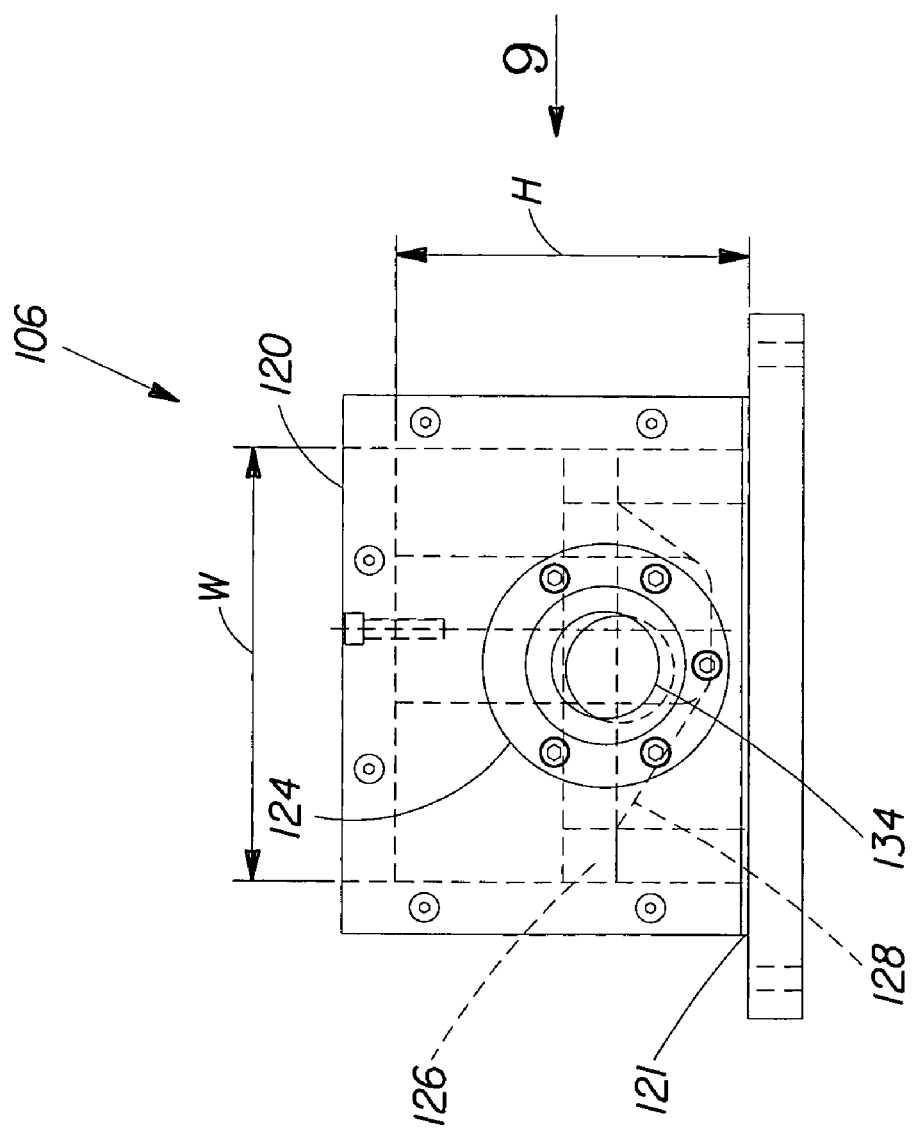
FIG. 7 is a front elevation view of the in vitro receptacle of FIG. 6, taken along lines 7—7 directed perpendicularly to the central axes 140 of the test stand, as shown in FIGS. 4 and 5.

Referring to FIGS. 3–5, the test apparatus 100 comprises a transparent base 102 disposed atop a diffuse light box 104 for transmitting the light from the light box 104 through the transparent base 102. The base 102 also serves for mounting the components of the test apparatus 100. These components include the following.

(1) An in vitro receptacle 106 for accepting a tampon provided by the deployment of a tampon-and applicator system being tested by the method of the present invention, wherein the receptacle 106 has transparent walls enable a test operator to view and/or photograph the position of the tampon inside the receptacle 106 after the deployment. The in vitro receptacle 106 is disclosed in detail below.

(2) An activation mechanism 108 for providing a consistent action for deploying the tampon from the tampon-and-applicator systems tested by the method of the present invention. The mechanism 108 pushes the smaller tube of the applicator of the tampon-and-applicator system tested to deploy the tampon, pushing the tampon a certain distance through the larger insertion end of the larger tube of the applicator at a controlled speed. Although the step of removing the empty applicator after the deployment of the tampon can be performed manually, the exemplary embodiment provides for more consistent removal procedure including two controlled steps (a) dwelling the tampon in the deployed position for a certain time inside the in vitro receptacle 106, and (b) removing the empty applicator from the in vitro receptacle 106 by way of removing an adapter (described below) holding the applicator.

(3) A photo camera 112 with a camera stand 110 for placing the camera 112 above the receptacle 106 for taking photographs of the deployed tampons inside the receptacle 106.

FIGS. 6–10 show one exemplary embodiment of the in vitro receptacle 106, which includes a container 120. The container 120 can be of any suitable shape and/or size, having transparent at least two walls: the top wall and the bottom wall, to enable a test operator to view and/or to photograph through the top wall the contents of the container 120 illuminated through the bottom wall by the light box 104 shown in FIGS. 3–5. However, in the exemplary embodiment of FIGS. 6–9, all walls of the container 120 are transparent and made of a 12 mm LEXAN. The walls are assembled to provide hermetic seal to withstand a pressure of at least 2.5 psi (17.2 kilopascal). In the shown embodiment, the bottom wall is removable to provide access inside the box, and includes a gasket 121 disposed between the bottom wall and the vertical walls to ensure hermetic seal. The inside dimensions of the exemplary embodiment of the container 120 are selected to have a width W of about 100 mm, a length L of about 106 mm, and a height H of about 82 mm.

The in vitro receptacle 106 further includes a flange 124 attached to the front wall of the container 120 at an opening 122 in the front wall of the container 120. The flange 124 enables for consistent positioning of the tampon-and-applicator systems tested by the method of the present invention, by providing both a certain direction and a depth of insertion of the applicators into the in vitro receptacle 106 during the deployment of the tampon into the in vitro receptacle 106.

Figure 8:
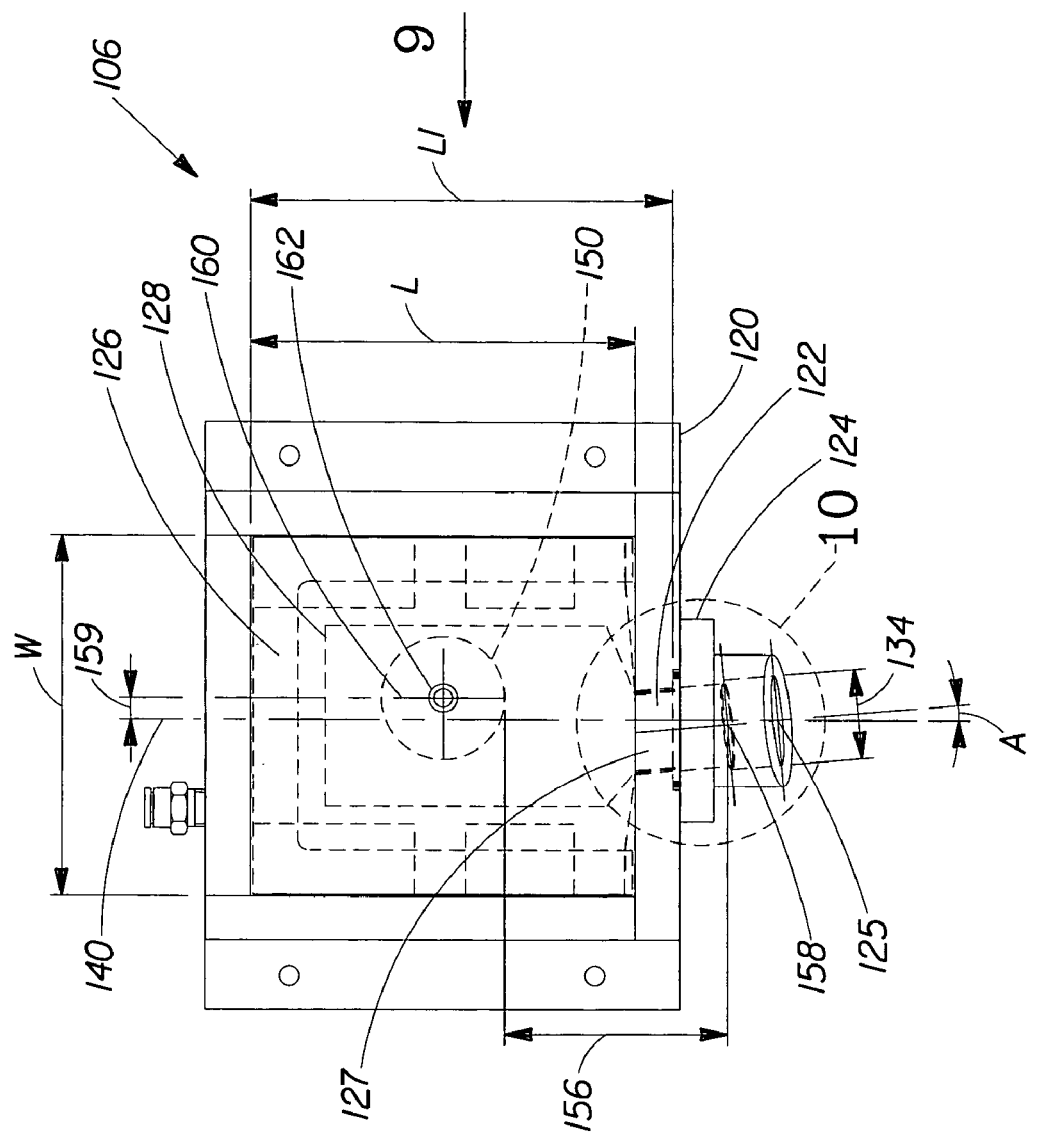
FIG. 8 is a top plan view of the in vitro receptacle of FIG. 7.
Figure 9:
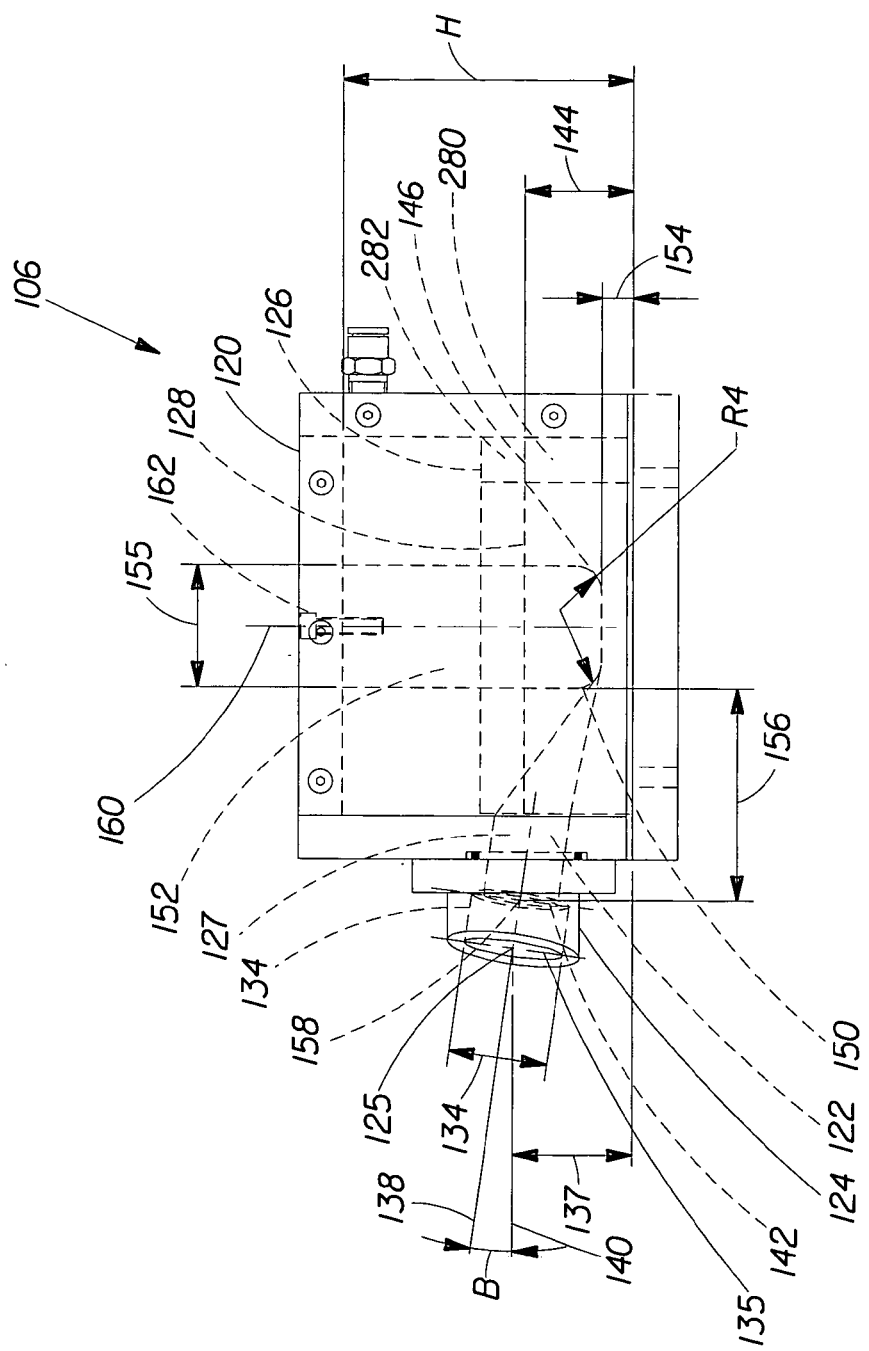
FIG. 9 is a side elevation view of the in vitro receptacle of FIGS. 7 and 8, taken along line 9.

The direction of insertion of the applicators of the tampon-and-applicator systems tested by the method of the present invention is selected by the applicants based on extensive testing by the applicants of female panelists using various tampon-and-applicator systems. The direction of insertion forms a horizontal angle A of 2 degrees in the horizontal plane, as shown in FIGS. 4 and 8, and a vertical angle B of 8 degrees in the vertical plane, as shown in FIGS. 5 and 9. However, it should be noted that within the scope of the present invention, the angles A and B can vary to represent different insertion conditions, if desired.

The direction of insertion is defined by the direction of a flange axis 138 forming the above angles A and B and extending through two openings (best shown in the enlarged view of FIG. 10): a larger opening 134 and a smaller opening 136, both of which being disposed concentrically in relation to the flange axis 138.

The two openings 134 and 136 are apportioned by a base surface 142 representing the position of a human hymenal ring at the entrance of the vagina. The base surface 142, as will be described in more detail below, provides for consistent depth of insertion of the applicators of the tampon-and-applicator system tested by the method of the present invention. The base surface 142 is perpendicular to the flange axis 138 and parallel to the front surface 135 of the flange 124. The base surface 142 is disposed at a depth D (FIG. 10) of 14 mm from the front surface 135.

The flange 124 is attached to the front wall of the container 120 such that the flange axis 138 coincides with the axis of the entry opening 122 of the container 120 and forms the above noted horizontal angle A (FIGS. 8 and 10) with a central axis 140 of the container 120. The central axis 140 equally divides the inside width W of the container 120. The central axis 140 also represents the axis coinciding with the sagittal plane dividing the user's body in halves.

Figure 10:
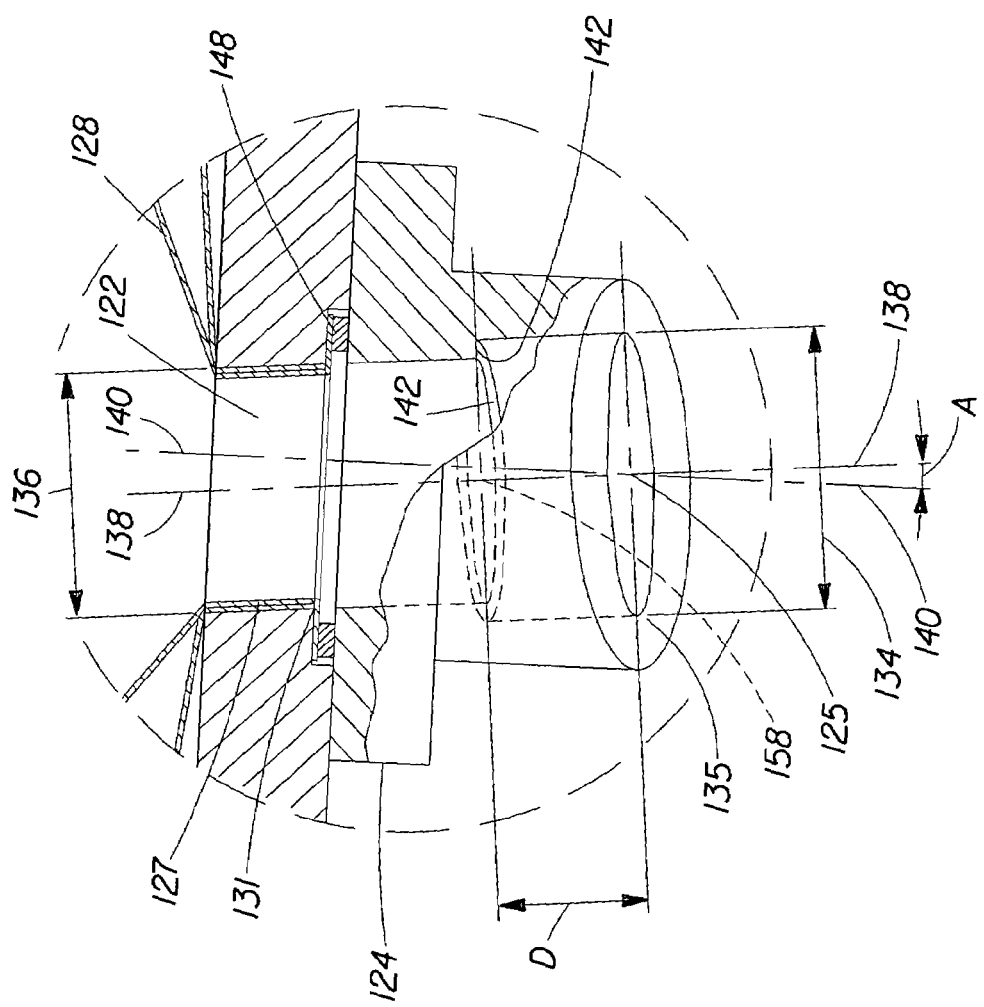
FIG. 10 is an enlarged, partly cross sectional, top plan view of the entry area of the in vitro receptacle shown in FIG. 8.
Figure 11:
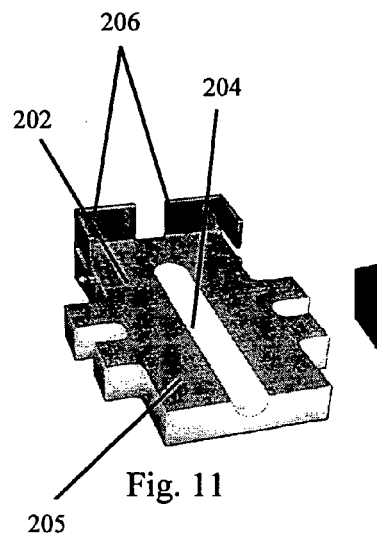
FIGS. 11–16 show photographs of the sequential stages of fabricating a sleeve of the in vitro receptacle of FIGS. 6–9, from two film sheets.

As best shown in FIG. 10, the flange axis 138 includes two points: a first point 125 and a second point 158 separated from each other by the depth D noted hereinabove. The first point 125 is aligned with the front surface 135 of the flange 124 and is the point of intersection of the flange axis 138 and the central axis 140. In the vertical plane, as shown in FIG. 9, the first point 125 is disposed at a height 137 of 33 mm from the bottom of the container 120. The second point 158 is aligned with the base surface 142 and is the point of intersection of the flange axis 138 with the plane of the base surface 142.

Figure 25:
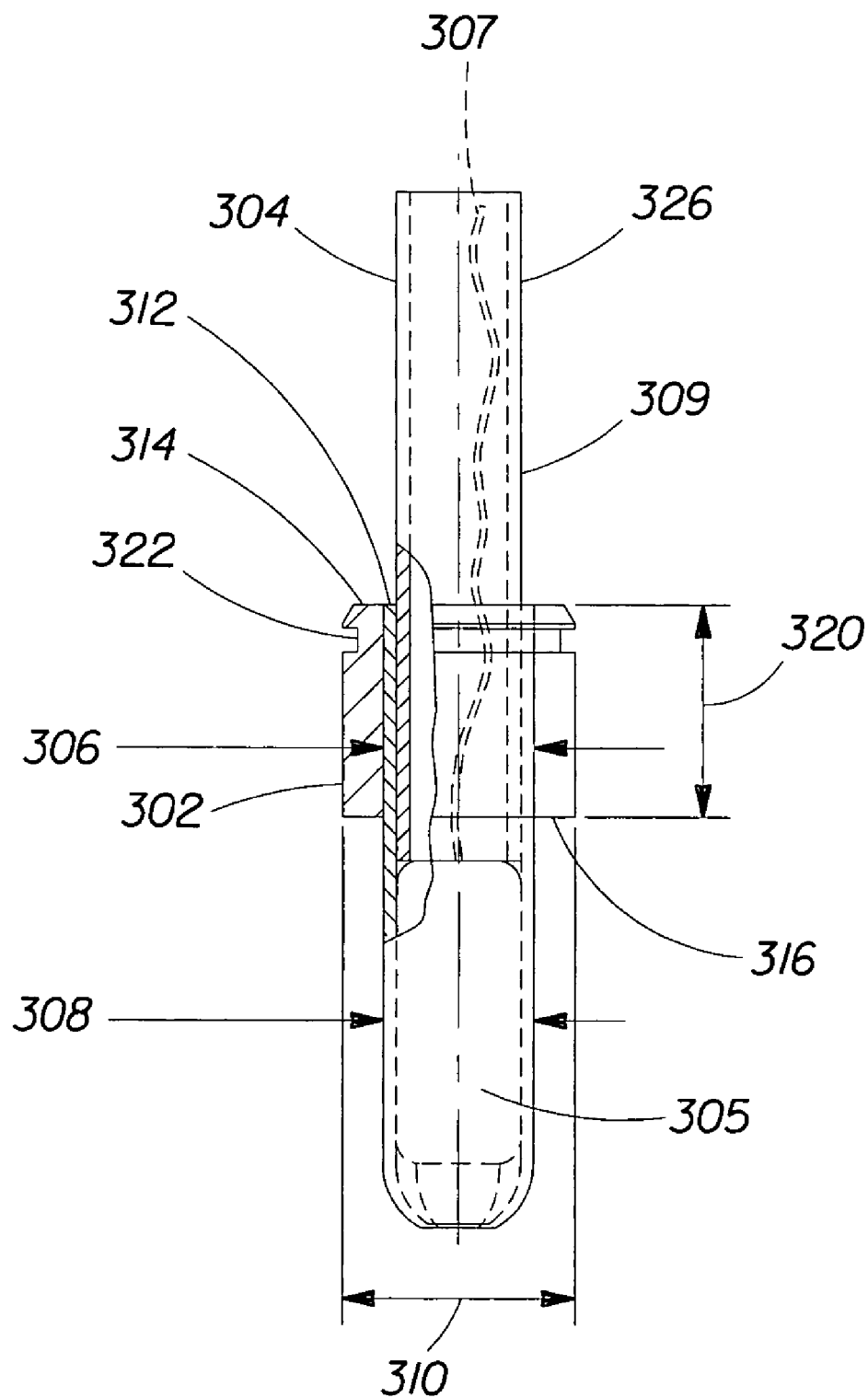
FIG. 25 shows one embodiment of an adaptor and a tampon-and-applicator system inserted into the adaptor.

The size of the larger opening 134 of the flange 124 is selected to be greater than the outer dimension of any tampon-and-applicator system to be tested by the method of the present invention. Moreover, because the outer dimensions of various tampon-and applicator systems to be tested by the method of the present invention can vary, the size of the larger opening 134 is selected to fit snugly the outer dimension of adaptors 302 (one embodiment of which is shown in FIG. 25) having the same outer dimension and different inner dimensions to fit various tampon and-applicator systems. In the exemplary embodiment of the present invention, the larger opening 134 is about 25 mm in diameter.

As shown in FIG. 25, the adaptor 302 can have an outer dimension defined by a diameter 310 of about 25 mm (sized to fit snugly into the larger opening 134 of the flange 124) and an inner opening 306 (which can be of any shape and size to fit snugly a larger tube 308 of an applicator 309 of a tampon-and-applicator system 304 to be tested by the method of the present invention). Accordingly, the method of the present invention can include a multiplicity of adaptors 302 having the same outer dimension 310 and different inner openings 306 designed to fit snugly different shapes and dimensions of different larger tubes 308 of different tampon-and-applicator systems to be tested by the method of the present invention.

The multiple adaptors 302 serve not only to fit different tampon-and-applicator systems, but also to provide for consistent positioning of different tampon-and-applicator systems with respect to the trailing end 312 (FIG. 25) of the larger tube 308 in the direction of insertion along the flange axis 138 (FIG. 10).

This consistent positioning of the tested tampon and applicator systems can be provided in the following manner. First, the tampon-and-applicator system 304 (FIG. 25) is inserted by the test operator into the adaptor 302 in such a manner that the trailing end 312 of the larger tube 308 is even with the trailing end 314 of the adaptor 302. Second, as will be also shown below, when the adaptor 302 with the tampon-and-applicator system inserted by the test operator into the larger diameter 134 of the flange 124, the leading end 316 of the adaptor 302 is brought against and in contact with the base surface 142 of the flange 124 to provide consistent positioning of the adaptor 302 along the flange axis 138.

As noted above, the multiple adaptors 302 can have different shapes of the inner openings 306 to accept different shapes and outer dimensions of the larger tubes of the tested tampon-and-applicator systems to provide for even positioning (as shown in FIG. 25) of the trailing end 312 of the larger tube 308 of different tampon-and applicator systems with the trailing end 314 of the different adaptors 302. For example, when a trailing end 312 of the larger tube 308 of a particular tampon-and-applicator system has a flange-like shape, the inner opening 306 of the adaptor 302 should have a recess to accommodate the flange-like shape of the larger tube 308 to provide for even positioning of the trailing end 321 of the larger tube 308 and the trailing end 314 of the adaptor 302.

Further, the multiple adaptors 302 have the same length 320 of about 23 mm to provide for consistent positioning of the tampon-and-applicator systems. The outer surface of the multiple adaptors 302 includes a circular grove 322, disposed adjacent the trailing end 314, for engaging with a driving member 356 (discussed below) of the activating mechanism 108 for pulling the adaptor 302 from the in vitro receptacle 106.

Figure 19:
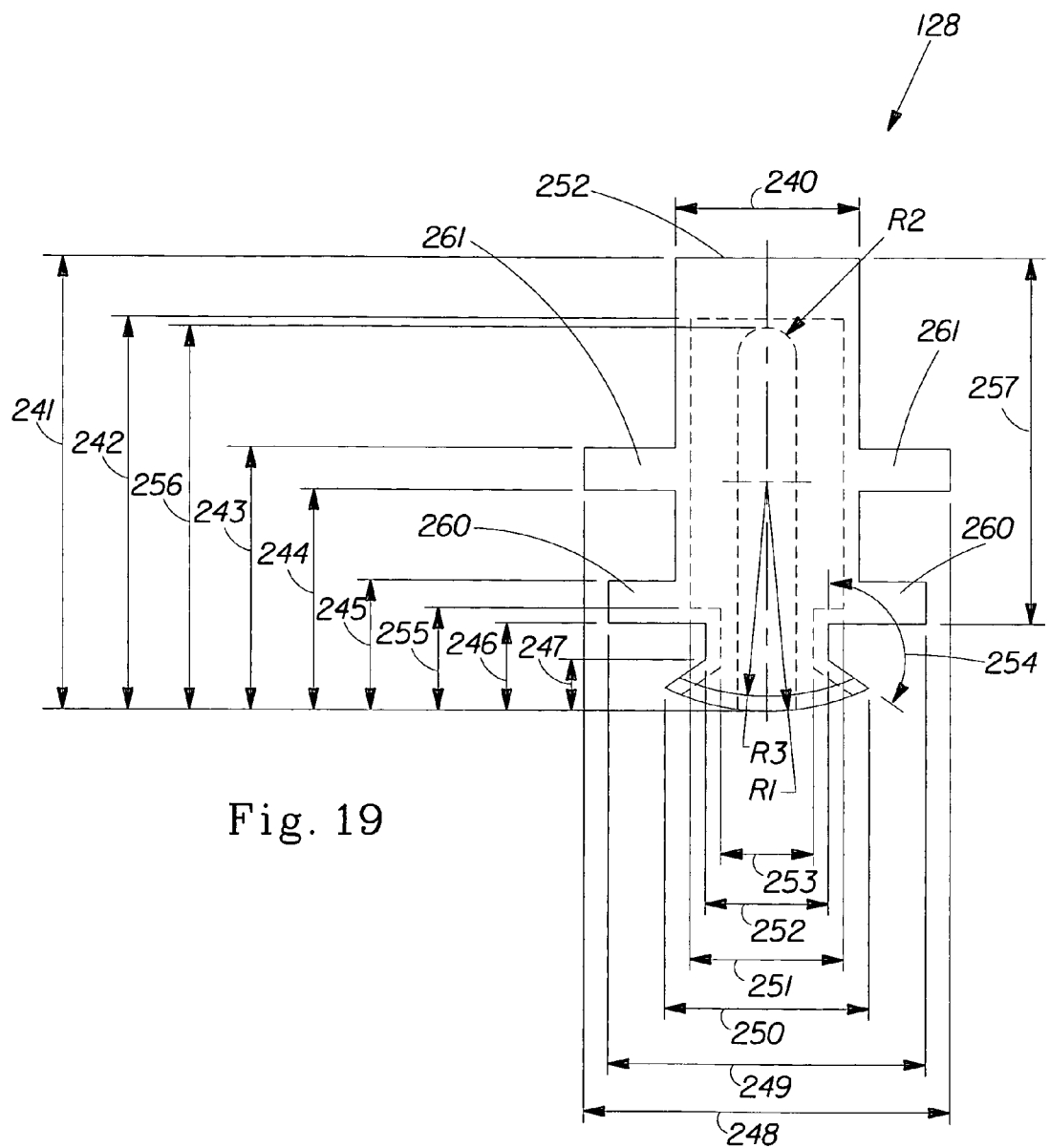
FIG. 19 is a top plan view of the sleeve trimmed by the trimming die of FIG. 18.
Figure 20:
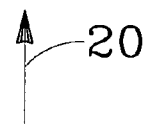
FIG. 20 is a side elevation view of the sleeve of FIG. 19, taken along line 20.

Referring again to FIGS. 6–9, the in vitro receptacle 106 further includes a sleeve 128, also shown separately in FIGS. 19 and 20, representing a human vaginal cavity. The sleeve 128, as shown in FIGS. 11–17, can be fabricated from two film sheets by sealing the two film sheets together to form a channel and then trimming the sealed sheets to form a desired outer contour.

Both film sheets can be of the same material characterized by relatively low gage, high stiffness and toughness, having a seal layer designed to offer a lock up seal strength when sealed at increased temperatures. It is important that film does not permanently distort during repeated tampon insertions. It is also important that the film not be so elastic as to cause the tampon to spring back once it is deployed in the sleeve 128. Such suitable film is identified as B559P-BX126B is HDPE/LLDPE/EVA coextruded film and provided by Printpack Inc., a division of Jackson Blown Film of Jackson, Tenn., has the properties shown in Table 1 below.

TABLE 1

| Properties | Units | ASTM #/ TAPPI # | Typical Value |
| --- | --- | --- | --- |
| Caliper | mil | TAPPI #411 | 1.15 |
| Basis Weight | Lbs/ream | TAPPI #410 | 16.80 |
| Yield | Sq. in/lb | | 25728 |
| Heat Seal Strength @ 200 deg. F./40 psi/sec | Lbs/in | | 1.25–3.0 |
| Tensile Strength | Psi MD | D882 | 4,000 |
| | CD | | 3,000 |
| Elongation at Break | % MD | D882 | 300 |
| | CD | | 450 |
| Tear Strength | Grams MD | D1983 | 75 |
| | CD | | 1100 |
| Coefficient of Friction In/In | gms | D1894 | 0.30 |
| Coefficient of Friction Out/Out | gms | D1894 | 0.25 |

Figure 16:
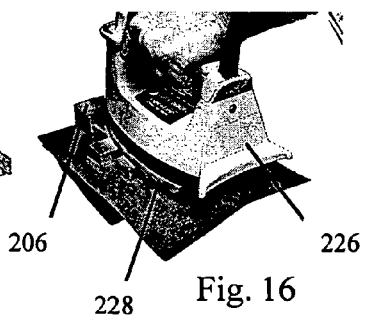
Figure 17:
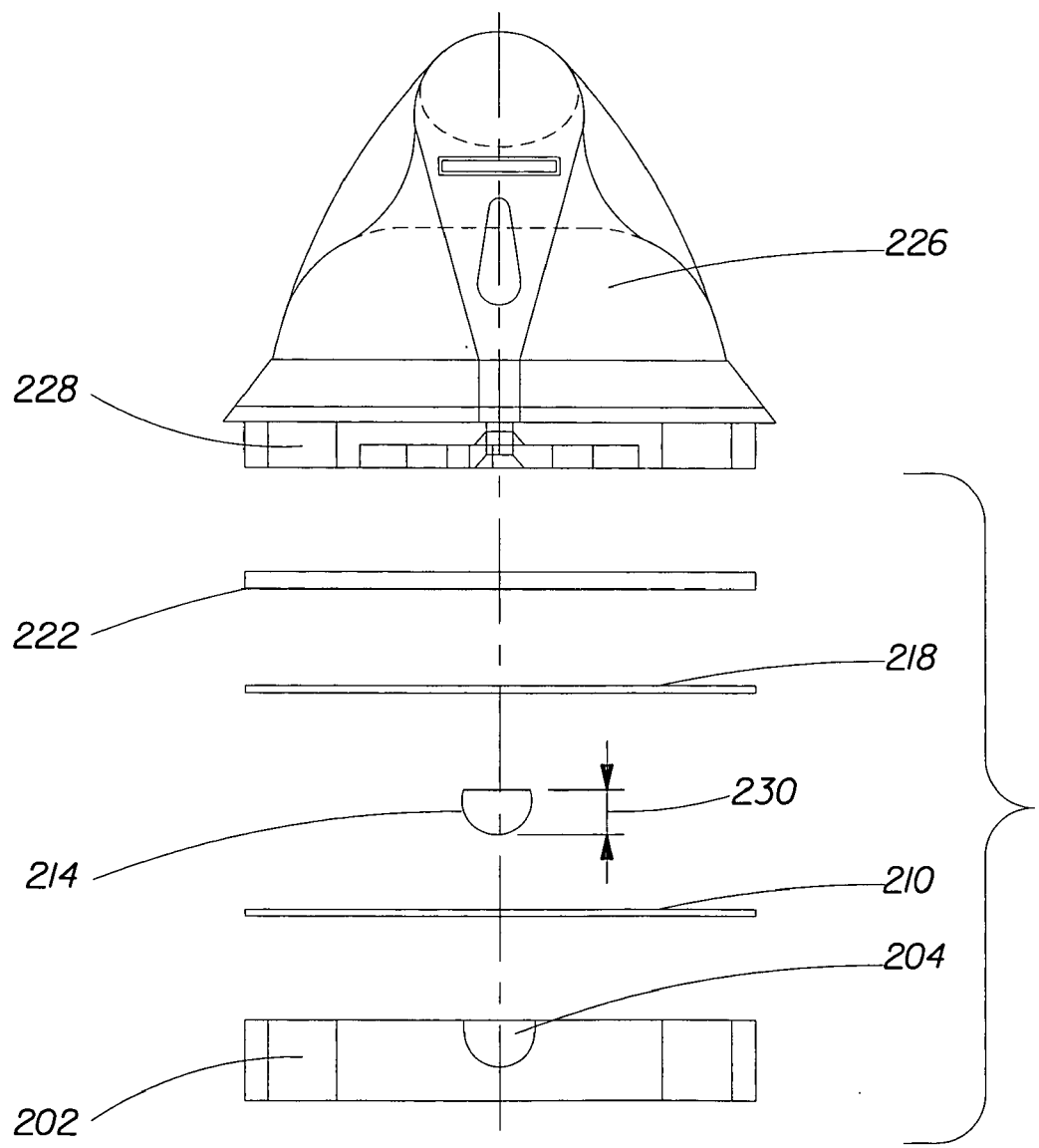
FIG. 17 is an assembly view of the components included in the sequential steps of fabricating the sleeve, as shown in FIGS. 11–16.

Referring again to FIGS. 11–16 showing photographs demonstrating the sequential steps of fabricating the sleeve 128 and to FIG. 17 illustrating the stack up order of the components shown in the photographs of the FIGS. 11–16, wherein FIG. 11 shows a lower sealing plate 202 made of NYLON with a cavity 204 machined with a 0.75" (19 mm) ball mill. The cavity 204 is about 5.6" (142 mm) long and about 0.51" (13 mm) deep to accommodate a bar 214 shown in FIG. 13. The bar 214 can be fabricated from a standard 0.750" (19 mm) diameter, 304 steel rod, machined to form a dimension 230 (FIG. 17) of about 0.490" (12.4 mm) to fit into the cavity 204 such that the bar 214 does not stick above the surface of the lower sealing plate 202.

The top surface 205 of the plate 202 is covered with a TEFLON coated FIBERGLASS fabric of 0.003" thick available from McMASTER-CARR #8577K81. The lower sealing plate 202 also includes guides 206 for providing proper positioning of an iron 226 shown in FIG. 16.

Figure 12:
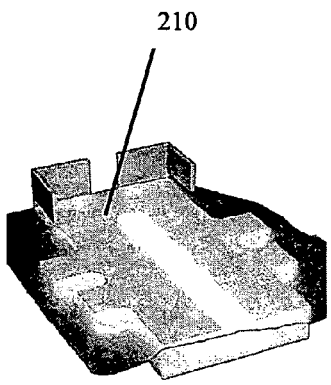

FIG. 12 illustrates the next step in the fabrication of the sleeve 128, showing a first film sheet 210 being placed on top of the lower sealing plate 202 such that the EVA side (referenced above with respect to the material for the sleeve 128) of the first film sheet 210 is facing up.

Figure 13:
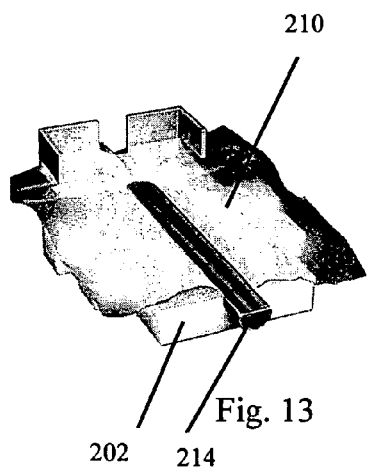

Further, FIG. 13 shows the bar 214 being placed on top of the first film sheet 210, thus forcing a portion of the first film sheet 210 to wrap under the bar 214 in the cavity 204.

Figure 14:
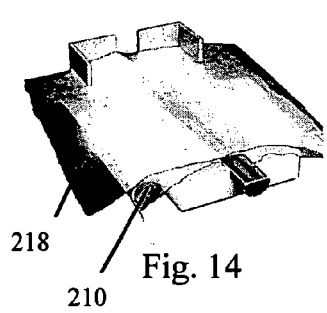
Figure 15:
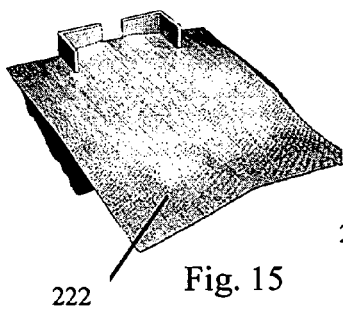

Further, FIG. 14 shows a second sheet 218 being placed on top of the first film sheet 210 such that the EVA side of the second film sheet 218 faces down toward the EVA side of the first film sheet 210. FIG. 15 shows a cover sheet 222 placed on top of the second film sheet 218. The cover sheet 222 can be a 5 mil TEFLON Sheeting #7755644120PPM08 available from Cincinnati Plastics of Cincinnati, Ohio.

Further, FIG. 16 shows an iron 226 attached to an upper sealing plate 228 (better shown in FIG. 17) being placed on top of the cover sheet 222 such that the guides 206 provide for proper positioning of the iron 226 and the upper sealing die 228. The upper sealing plate 228 is made of aluminum to provide for sufficient heat transfer. The iron 226, heated to about 270–290 degrees F. (231–143 degrees C.) is held in the sealing position for about 30 seconds and then removed to allow the materials to cool for about 2 minutes before removing the sealed together the first and second film sheets 210 and 218.

Figure 18:
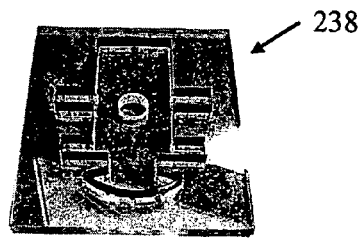
FIG. 18 is a photograph of a trimming die for trimming the periphery of the sleeve fabricated according to the steps shown in FIGS. 11–16.

As a final step in fabricating the sleeve 128, the sealed sheets 210 and 218 are trimmed in a trim die 238 shown in FIG. 18, to form the outer configuration of the sleeve 128, a plan view of which is shown in FIG. 19. FIG. 20 shows a side elevation view of the sleeve 128 of FIG. 19, taken along line 20. The outer dimensions forming the configuration of the sleeve 128 of FIGS. 19 and 20, provided by both the sealing and trimming operations described above, are shown in Table 2 below.

TABLE 2

| Identification in FIG. 19 | Dimension |
| --- | --- |
| 240 | 62 mm |
| 241 | 145 mm |
| 242 | 135 mm |
| 243 | 95 mm |
| 244 | 78 mm |
| 245 | 47 mm |
| 246 | 32 mm |
| 247 | 20 mm |
| 248 | 123 mm |
| 249 | 117 mm |
| 250 | 67 mm |
| 251 | 50 mm |
| 252 | 35 mm |
| 253 | 29 mm |
| 254 | 125 degrees |
| 255 | 34 mm |
| 256 | 127 mm |
| 257 | 117 mm |
| R1 | 50 mm |
| R2 | 9.5 mm |
| R3 (marked line) | 38 mm |

After the fabrication of the sleeve 128, including the sealing and trimming steps described above, the sleeve 128 is inspected for pinholes using a suitable light table. A sleeve 128 containing any pinholes should be discarded.

Figure 21:
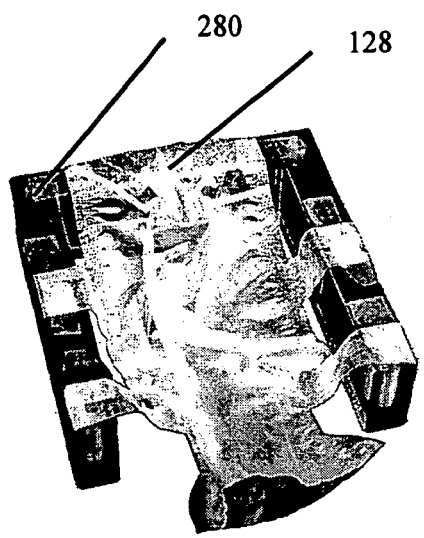
FIGS. 21–23 show photographs of sequential stages of assembling a sleeve assembly including the sleeve of FIGS. 19 and 20.
Figure 22:
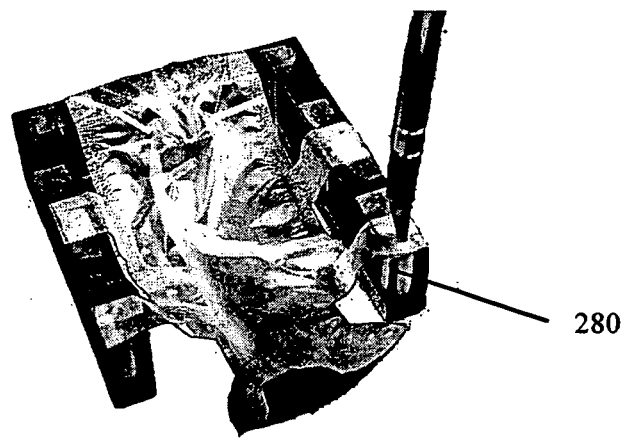
Figure 23:
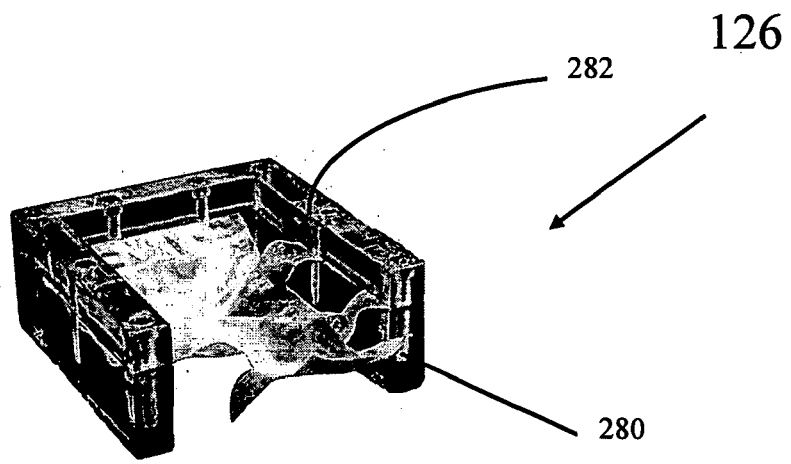
Figure 24:
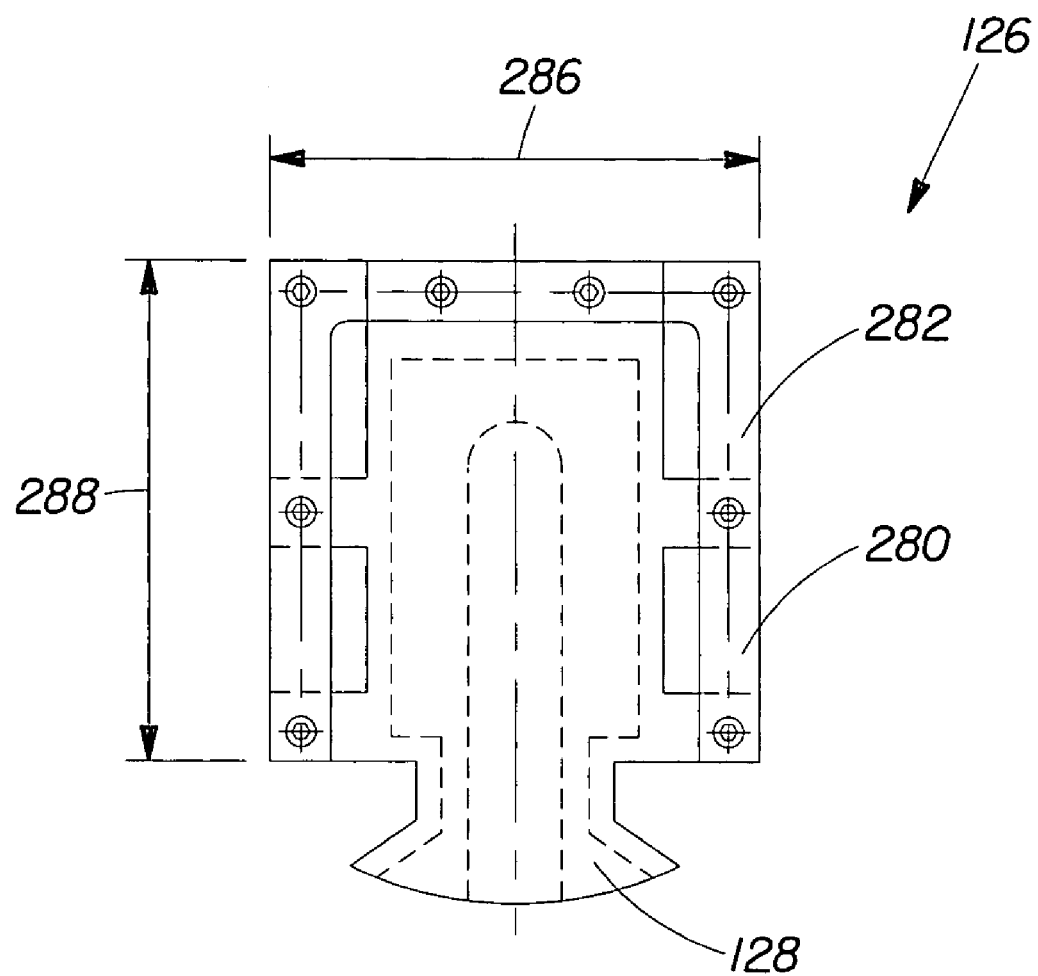
FIG. 24 is a top view of the assembled sleeve assembly shown in FIG. 23.

The sleeve 128 is then assembled into a sleeve assembly 126 comprising a lower frame 280, an upper frame 282, and the sleeve 128 clamped therebetween, according to FIGS. 21–23 described below. FIG. 24 shows a top plan view of the sleeve assembly 126 after completing the assembling steps of FIGS. 21–23.

As shown in FIGS. 21–24, the sleeve 128 is positioned within the upper and lower frames 280 and 282 of the sleeve assembly 126 such that the lateral edges of the first and second tabs 260 and 261 of the sleeve 128 and the back edge 252 of the sleeve 128 are even with the outer edges of the frames 280 and 282. It should be noted that the width 286 (FIG. 24) of the lower and upper frames 280 and 282 is about 100 mm, which is less than the first width 249 (FIG. 19) of about 117 mm between the lateral edges of the first tabs 260, and less than the second width 248 (FIG. 19) of about 123 mm between the lateral edges of the second tabs 261. Further, the length 288 (FIG. 24) of the frames 280 and 282 is about 106 mm, which is less than the length 257 (FIG. 19) of about 117 mm from the front edge of the first tab 260 to the back edge 252 of the sleeve 128. The above noted larger dimensions of the sleeve 128 in relation to those of the frames 280 and 282 have been selected to provide for the sleeve 128 to sag inside the frames 280 and 282, as shown in FIG. 9.

Referring to FIGS. 6–9, showing the sleeve assembly 126 inside the in vitro receptacle 106 and, specifically, inside the container 120, wherein the frames 280 and 282 of the sleeve assembly 126 fit preferably snugly inside the container 120 to prevent movement of the sleeve assembly 126 relative to the container 120. The sleeve assembly 126 is positioned at the bottom of the container 120 such that the sleeve opening 127 of the sleeve 128 faces the opening 122 in the front wall of the container 120, and the top surface 146 of the lower frame 280 of the sleeve assembly 126 forms a distance 144 of about 30 mm with the bottom of the container 120.

As best shown in FIG. 10, the sleeve 128 is assembled with the opening 122 of the container 120 such that the sleeve 128 is drawn through the opening until the marked line of the radius R3 (FIG. 19) coincides with the circular edge 131 of the opening 122. The sleeve 128 is clamped under a gasket 148 surrounding the opening 122 of the container 120 and the flange 124 affixed to the container 120.

Referring again to FIGS. 6–9, the in vitro receptacle 106 further includes a tampon deflecting area 150 inside the sleeve 128, representing the frontal area 19 (FIG. 1) of the cervix 18 inside a human vagina. In the exemplary embodiment of the present invention, the tampon deflecting area 150 is provided by a column 152 pressing on the upper sheet of the sleeve 128. However, within the scope of the present invention, the tampon deflecting area 150 can be provided by any suitable means capable of deflecting a deployed tampon inside the sleeve 128, including any suitable means inside the sleeve 128 (e.g., a sealed area combining the top and bottom sheets of the sleeve 128 to form a deflecting area 150) or outside the sleeve 128, one example of which is represented by the column 152.

In the exemplary embodiment of the present invention, the column 152 extends vertically and forms a distance 154 of about 10 mm between the bottom of the column 152 and the bottom of the container 120. The column 152 is selected to have a cylindrical shape with a diameter 155 of about 34 mm and a radius R4 of about 6 mm at the bottom of the column 152.

In the vertical plane, as shown in FIG. 9, the outer surface of the column 152 forms a distance 156 of about 59 mm with the second point 158 noted above as being aligned with the base surface 142 and being the point of intersection of the flange axis 138 with the plane of the base surface 142. In the horizontal plane, as shown in FIG. 8, the column 152 is offset in relation to the central axis 140 of the container 120, forming a distance 159 of about 5 mm between the central axis 140 and the column axis 160.

The column 152 is made by molding a silicone rubber having a shore hardness of about 25A, available from Silicones, Inc. of High Point, N.C., under the name of GI-1000A. The column 152 is fastened to the top of the container 120 by a screw 162, which axis coincides with the column axis 160. The screw hole of the column 152 includes a metal insert molded into the top of the column 152 to prevent the column 152 from tearing.

Referring to FIGS. 8–9, the in vitro receptacle 106 further includes a port pressurizing the container 120 from about 0 to about 2.5 psi (17.2 kilopascal) above the ambient atmospheric pressure by compressed air. Pressurizing the container 120 creates pressure around the sleeve 128, creating resistance to the entering tampon, simulating the resistance to the tampon entering a human vagina.

Referring again to FIGS. 3–5, which show the activation mechanism 108 for providing the action of deploying a tampon from the applicator tube of the tampon-and-applicator systems tested by the method of the present invention. In this action, the activation mechanism provides a forward stroke of an air cylinder rod pushing the smaller tube of the applicator deploying the tampon from the larger tube of the applicator. The length of the stroke, as well as the speed of the advancing rod, can be reset by any suitable means known in the art, for different tampon-and-applicator systems to be tested by the method of the present invention.

The activation mechanism can perform also other actions, which can be performed manually, but are preferably included in the disclosed embodiment. One action is halting the air cylinder rod in its extended position for a certain time, 8–10 seconds, set by any suitable means. The other action is the retraction of the air cylinder rod pulling the empty tampon applicator from the in vitro receptacle after the deployment of the tampon into the in vitro receptacle 106.

As shown in FIGS. 3–5, the activation mechanism 108 includes an air cylinder 350 attached to the base 102 of the test apparatus 100 by a suitable bracket 352 in such a way that to form two angles noted above: the horizontal angle A (FIG. 4) in the horizontal plane and a vertical angle B (FIG. 5) in the vertical plane.

Figure 29:
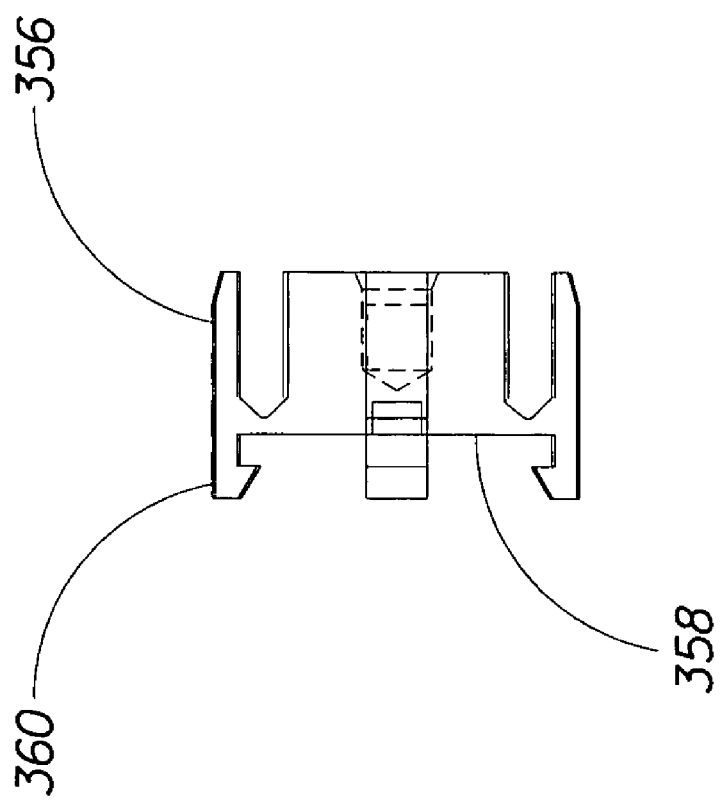
FIG. 29 is an enlarged side elevation view of the activation member of FIG. 28.

The air cylinder 350, when activated, extends a rod 354 having at its end a drive member 356 comprising a relatively smooth surface 358 oriented perpendicularly to the air cylinder axis, for contacting and pushing the smaller tube of tampon applicator to deploy a tampon. However, in addition to providing the pushing action for deploying the tampon, the drive member 356 of the disclosed embodiment is also designed to provide a pulling action for removing the adaptor 302 with the empty tampon applicator from the in vitro receptacle 106 after the deployment of a tampon. For this, the drive member 356 includes flexible grippers 360 (FIG. 29) designed to engage with a circular grove 322 (FIG. 25) of the adaptor 302.

The speed at which the drive member 356 pushes the smaller tube 326 is about 60 mm per second. The retraction speed of the drive member 356 can be any reasonable speed. Both speeds can be provided by any suitable means commonly used in the art.

After pushing the smaller tube 326 of the applicator, the air cylinder 350 remains in the extended position, dwelling for a selected time of about 8–10 seconds before retracting. The air cylinder 350 can be any suitable air cylinder, for example a ¾" bore Clippard Minimatic, Part # M3 UDR-12-4 obtained from Clippard Instrument Laboratory, Cincinnati, Ohio. The operation of the air cylinder for providing a desired stroke (about 72 mm), speed (about 60 mm/sec), and dwelling time (about 8–10 seconds) can be provided by any suitable means known in the art.

Figure 30:
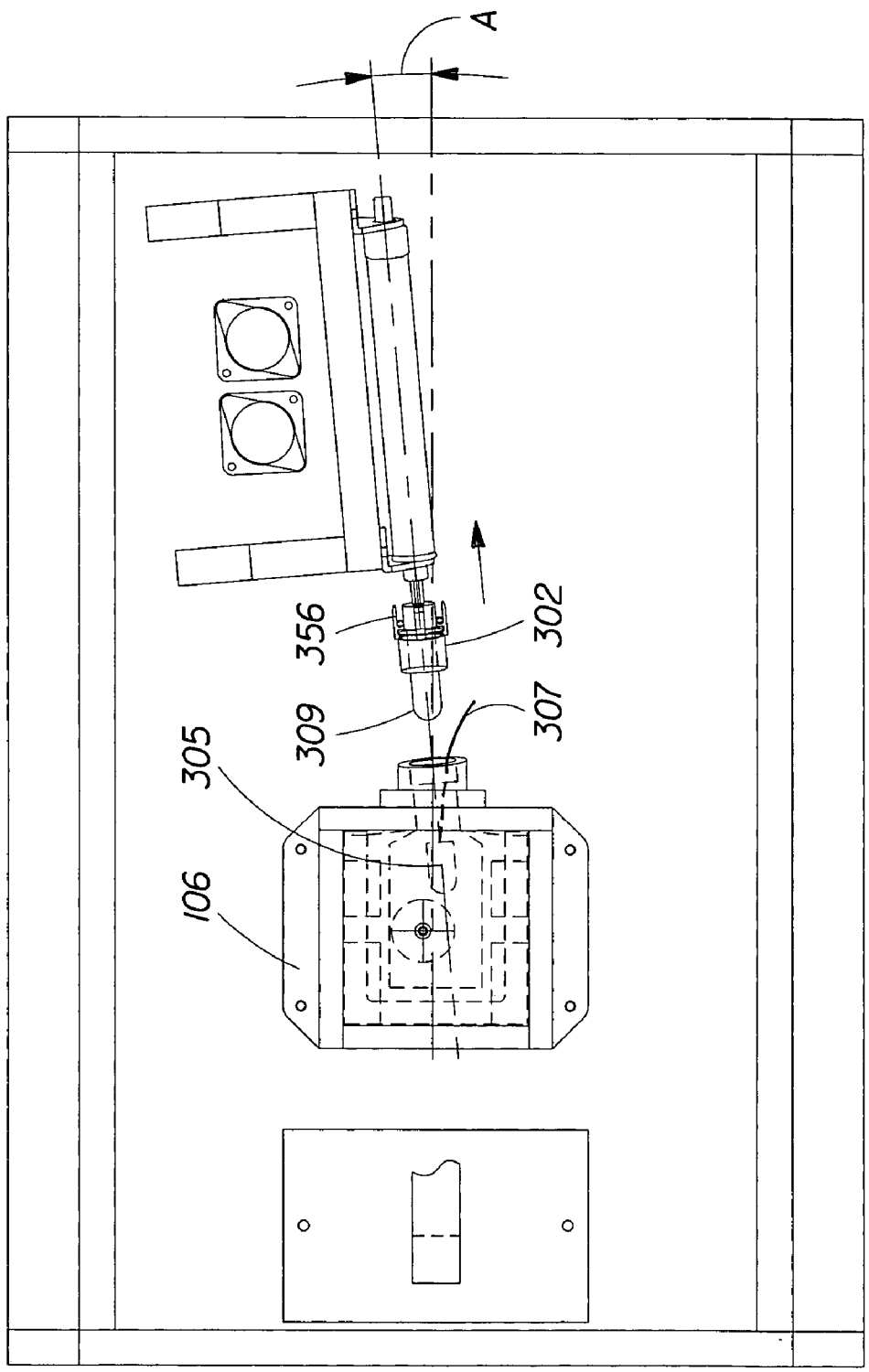
FIG. 30 is a top plan view of the test stand of FIG. 28, showing the retraction action of the activation mechanism with the activation member pulling the adaptor with the empty applicator from the in vitro receptacle.

After the removal of the adaptor 302 with the empty applicator 309, a pin plug 370 (as shown in FIG. 30) is inserted by the operator into the in vitro receptacle 106 to provide a reference point coinciding with the second point 158 noted above.

Figure 32:
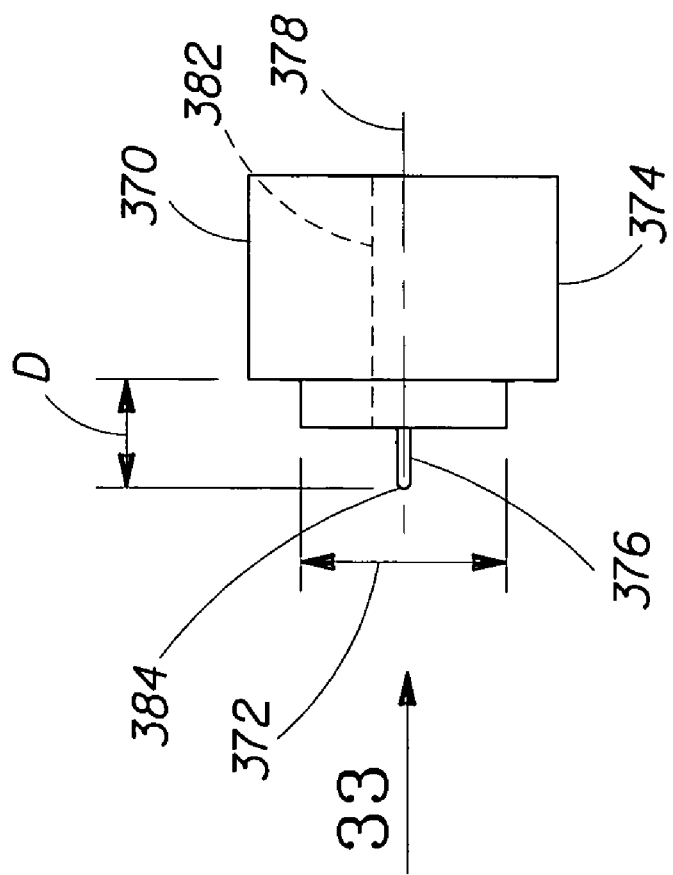
FIG. 32 is an enlarged elevation view of the pin plug of FIG. 31, taken along lines 31—31 disposed parallel to the direction of insertion 138.
Figure 33:
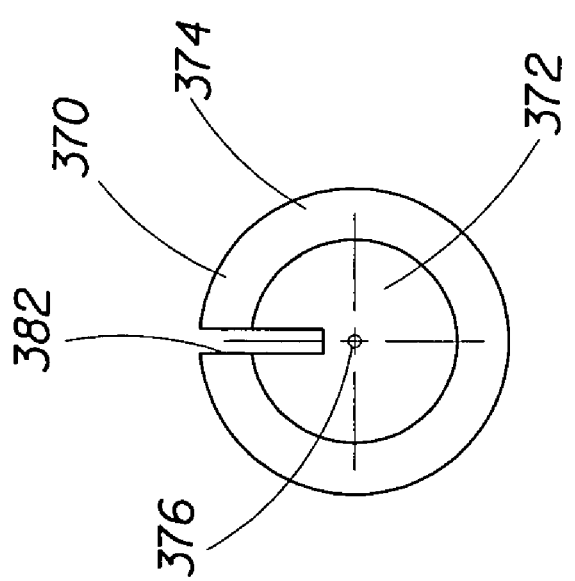
FIG. 33 is an enlarged side view of the pin plug of FIG. 32, taken along arrow 33.

As shown in FIG. 32, the pin plug 370 has a smaller cylinder 372, a larger cylinder 374, a pin 376 extending along the axis 378 at a distance D of 14 mm from the larger cylinder 374, and a slot 382 extending through the both cylinders 372 and 374. The diameter of the smaller cylinder 372 is sized to fit snugly into the larger opening 134 (FIG. 9) of the in vitro receptacle 106. The diameter of the larger cylinder 374 can be of any size that is larger than that of the smaller cylinder to provide for the predetermined depth D of insertion of the tip 384 of the pin 376. At that depth D of insertion, the position of the tip 384 of the pin 376 coincides with the second point 158 on the flange axis 138 of the flange 124. The position of the tip 384 serves herein as a basis point for measuring the position of the anterior boundary 404 of the target positioning zone 400 (described below) disposed horizontally inside the transparent walls of the in vitro receptacle 160 for viewing and/or photo graphing from above the container 120.

A suitable photo camera 112 (such as CANNON EOS Digital Rebel, 6.3 Megapixel, Interchangeable Lense, SLR, Digital Camera with Cannon Normal EF 50 mm f/2.5 Compact Macro Autofocus Lens USA, Mfr. Catalog # 2537A003, B&H Catalog # CA5025MEF) is disposed on the bracket 110 at a distance 107 of about 297 mm measured between the top of the in vitro receptacle 106 and the bottom surface of the focused lens. The measurements may be calibrated by using a plastic cylinder representing a tampon deployed into the in vitro receptacle 106. For example, the plastic cylinder can be made of TEFLON), having a diameter of about 16 mm and a length of about 50 mm.

It should be noted that the characteristics selected for designing the test apparatus of the present invention have been based on the data collected by the applicants from the dozens of panelists. Table 3 below shows some of the characteristics and their representation in the particular embodiment of the test apparatus disclosed herein.

TABLE 3

| Measurements of Panelists | IN VIVO Range measured, mm | Denotation #, FIG. # | IN VITRO Dimension, mm |
|---|---|---|---|
| A longitudinal distance between Hymenal Ring and the frontal area of Cervix | 40–70 | 156, FIGS. 8, 9 | 59 |
| A lateral misalignment between the center of Cervix and the central axes of Hymenal Ring | 0–12 | 159, FIG. 8 | 5.25 |
| A diameter of Cervix | 30–40 | 155, FIG. 9 | 34 |
| Vaginal channel width at Cervix | 30–60 | 251, FIG. 19 | 50 mm when sleeve 128 is flat and about 45 mm when it |

TABLE 3-continued

| | IN VIVO | | |
|---|---|---|---|
| | Range | IN VITRO | |
| Measurements of Panelists | measured, mm | Denotation #, FIG. # | Dimension, mm |
| | | | forms a 3D profile under column 152, FIG. 9 |

Figure 34:
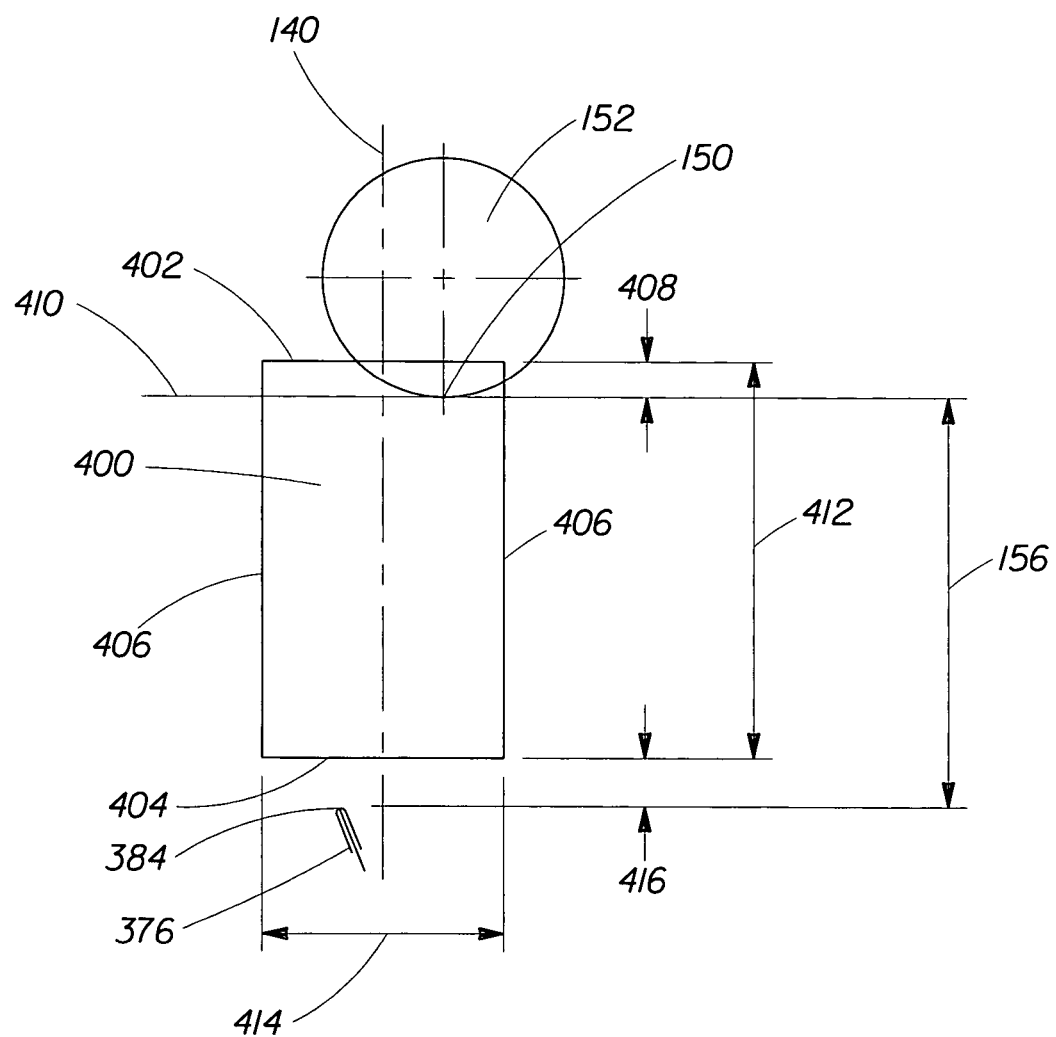
FIG. 34 is a schematic diagram illustrating the dimensional ranges of a low-placement positioning zone of the present invention.

FIG. 34 is a schematic diagram illustrating variable dimensions of a low-placement positioning zone 400 of the present invention disposed in a horizontal plane relative to both the deflecting zone 150 of the front area of the column 152 and the tip 384 of the pin 376 (disposed slightly off set from the central axis 140) of the pin plug 370 (not shown in FIG. 34). The low-placement positioning zone 400 defines a rectangular comprising a posterior boundary 402, an anterior boundary 404, and two opposing side boundaries 406 disposed symmetrically and parallel to the central axes 140 (also shown in FIGS. 7–10 of the in vitro receptacle 106). As noted above, the tip 384 of the pin 376 indicates the position of the second point 158 in the plane of the base surface 142.

The posterior boundary 402 of the low-placement positioning zone 400 is disposed at a posterior depth 408 measured from a line 410 drawn perpendicularly to the center line 140 and tangentially to the deflecting zone 150 of the column 132. The posterior depth 408 is preferably 0 mm and less preferably about 3 mm.

The anterior boundary 404 of the low-placement positioning zone 400 is disposed at an anterior depth 416 measured from the tip 384 of the pin 376. The anterior depth 416 is preferably about 10 mm, less preferably about 5 mm, and even less preferably 0 mm.

Accordingly, depending on the particular positions of the anterior and the posterior boundaries 410 and 402, the length 412 of the low-placement positioning zone 400 can range from about 49 mm (most preferred) to about 62 mm (least preferred). Further, the width 414 of the low-placement positioning zone 400 can also range from 30 to 40 mm.

Method Steps

Figure 26:
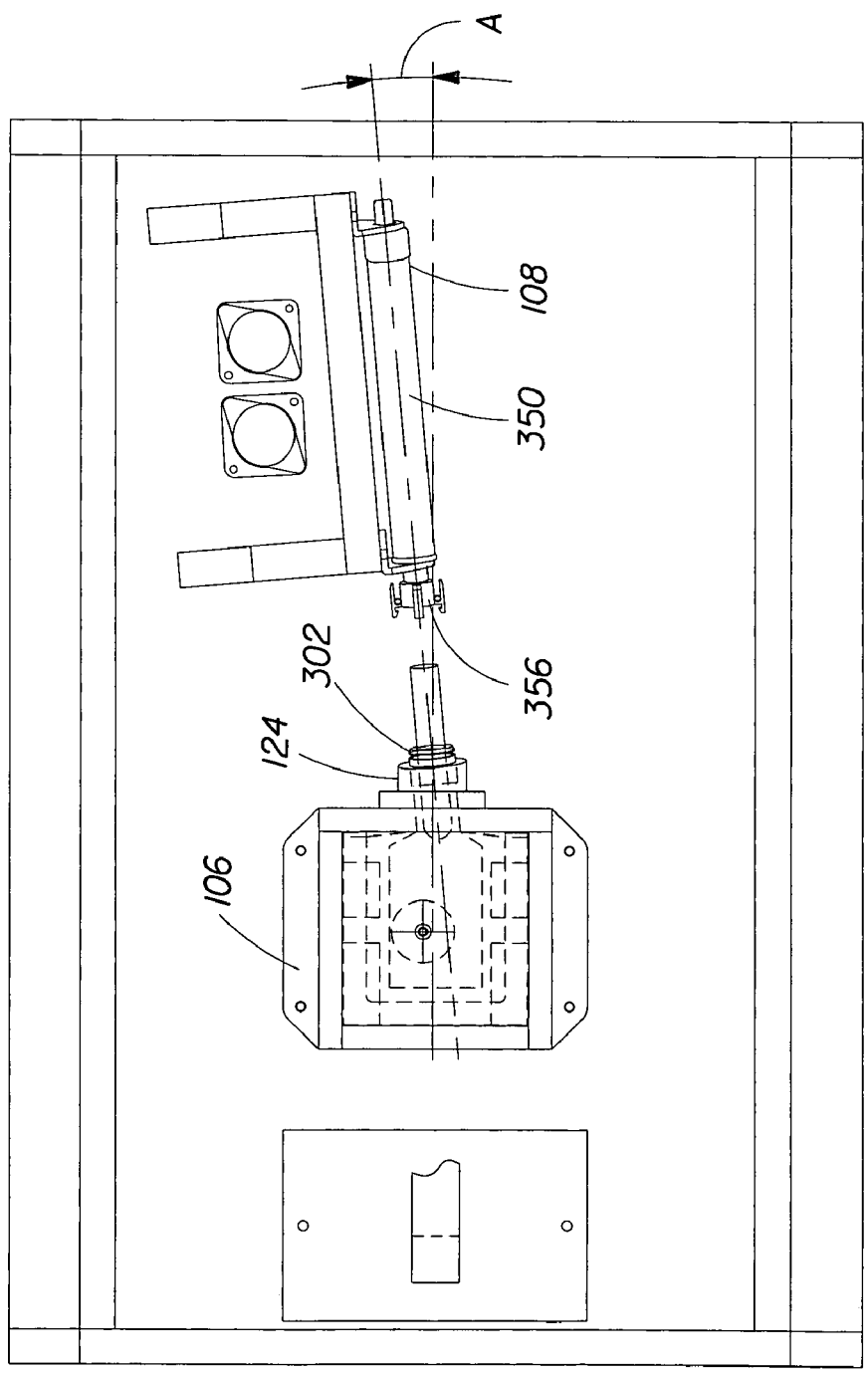
FIG. 26 is a top plan view of the test stand of FIG. 4, additionally showing the adaptor with a tampon-and-applicator system of FIG. 25, being inserted into the in vitro receptacle.
Figure 27:
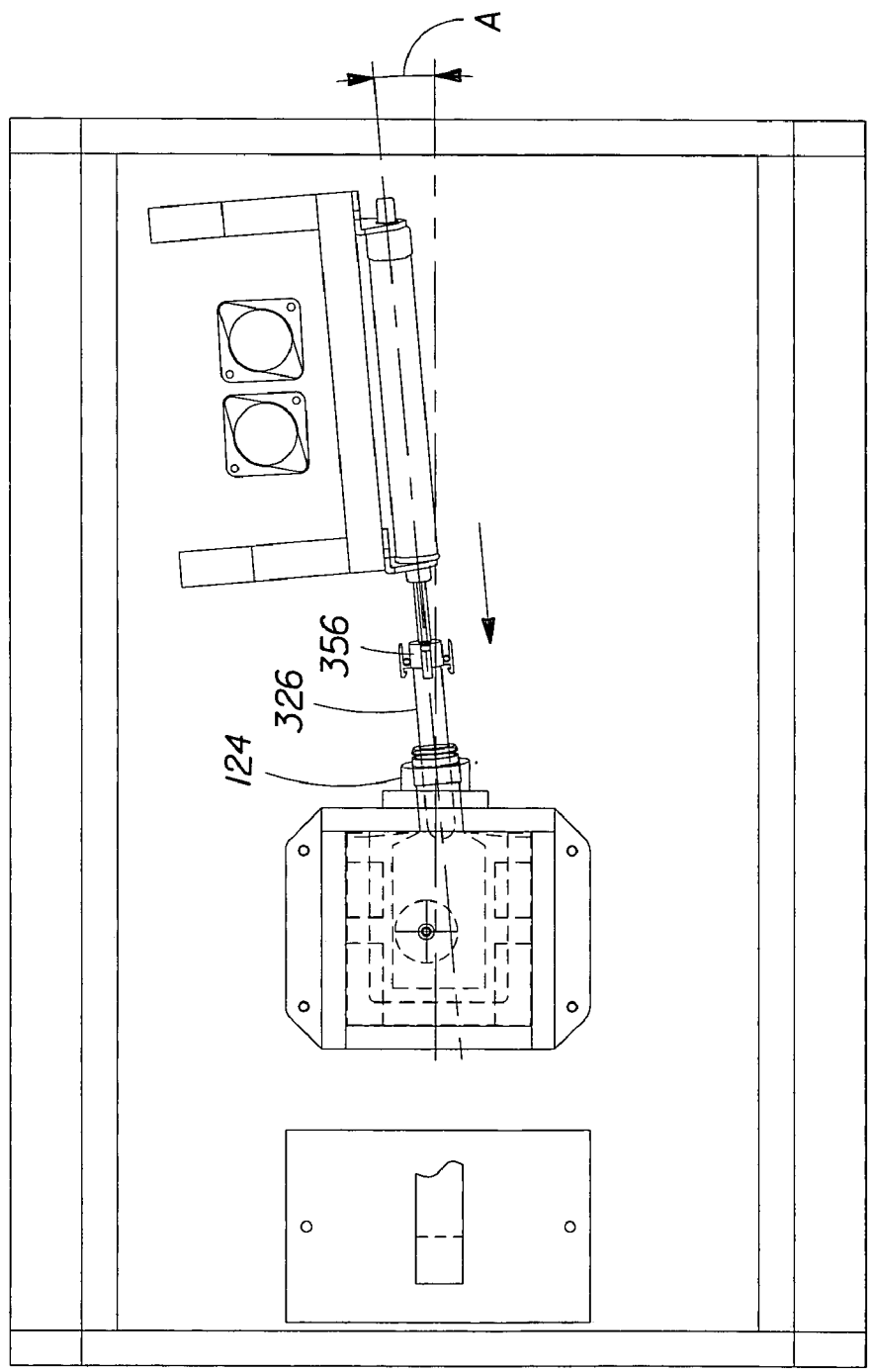
FIG. 27 is a top plan view of the test stand of FIG. 26, showing the initial forward action of the activation mechanism pushing the applicator to deploy the tampon into the in vitro receptacle.
Figure 28:
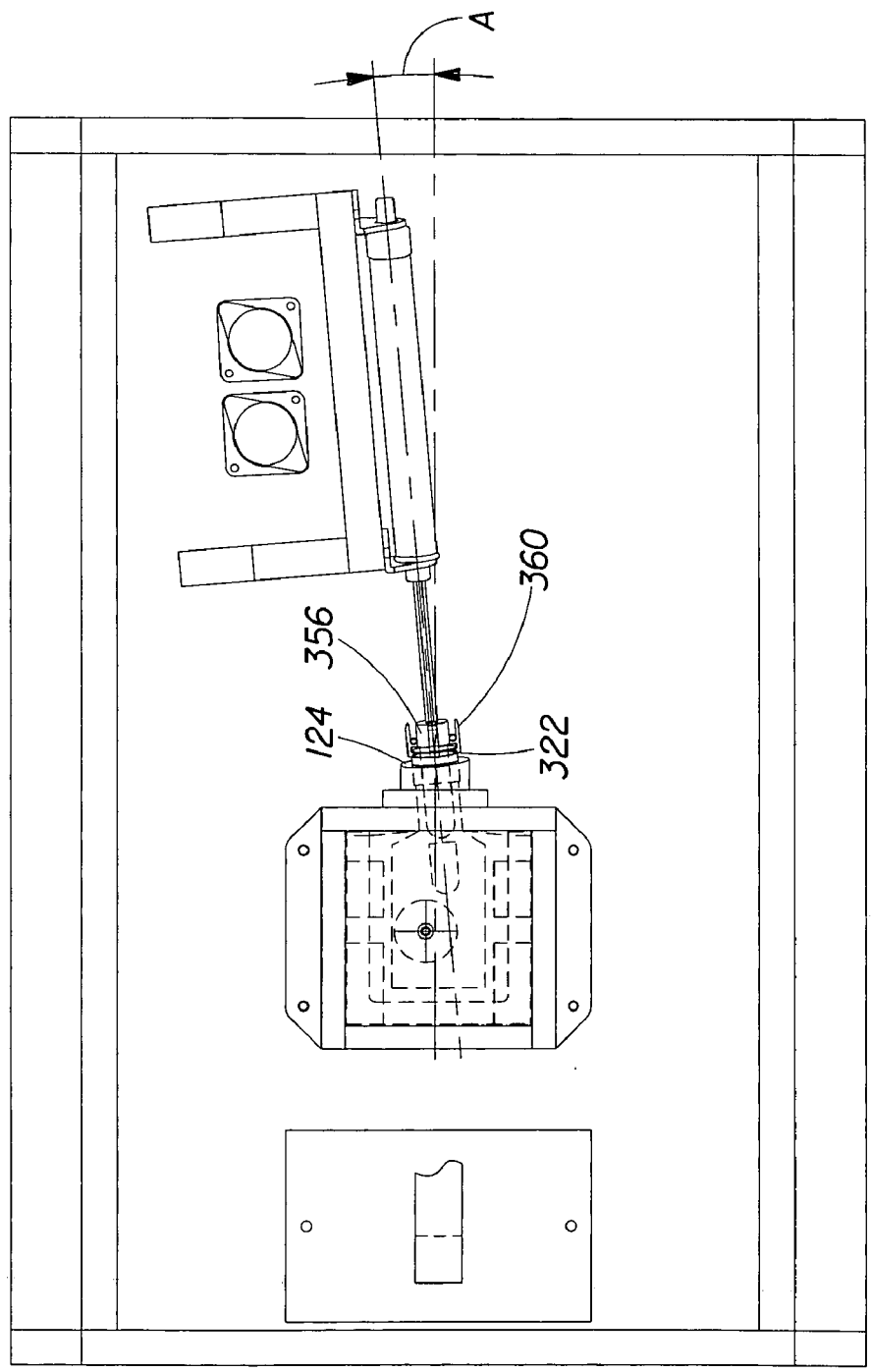
FIG. 28 is a top plan view of the test stand of FIG. 27, showing the competed forward action of the activation mechanism after the deployment of the tampon into the in vitro receptacle.
Figure 31:
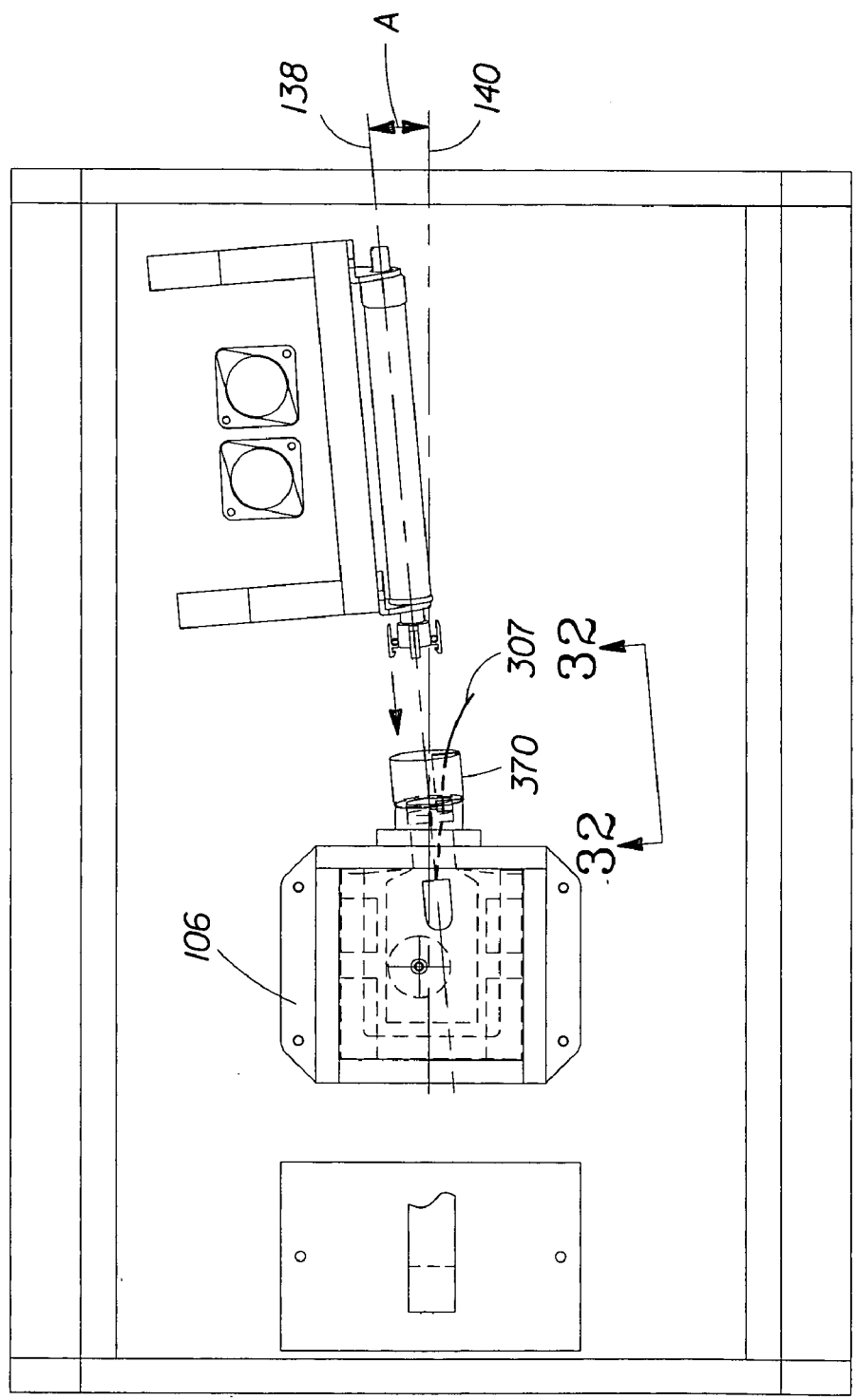
FIG. 31 is a top plan view of the test stand of FIG. 30, additionally showing a pin plug inserted into the vitro receptacle.

1) Pressurizing the container 120 of the in vitro receptacle 106 to provide an outer pressure of about 0.6 psi (4.1 Pascal) for the sleeve 128 inside the container 120.
2) Inserting a tampon-and-applicator system to be tested by the method of the present invention into the adaptor 302 (FIG. 25) such that the trailing end 312 of the larger tube 308 of the tested tampon-and-applicator system is even with the trailing end 314 of the adaptor 302.
3) Arranging a removal string 307 (FIG. 25) inside the smaller tube 326 so the removal string 307 is fully contained inside the smaller tube 326 and does not become subsequently entrapped between the smaller tube 326 and the drive member 356 (FIG. 4) of the activation mechanism 108.
4) Placing the adaptor 302 with the tampon-and-applicator system into the flange 124 of the in vitro receptacle 106, as shown in FIG. 26, such that the leading end 316 (FIG. 25) of the adaptor 302 is brought against and in contact with the base surface 142 (FIG. 9) of the flange 124. As shown in FIG. 26, the driving member 356 of the air cylinder 350 of the activating mechanism 108 is in a retracting position.
5) Activating the air cylinder 350 to advance the driving member 356 to push the smaller tube 326 to eject the tampon 305 from the tampon-and-applicator system. FIG. 27 shows the driving member 356 advancing to push the smaller tube 326. FIG. 28 shows the driving member 356 at the end of its advancing action deploying the tampon 305 into the in vitro receptacle 106.
6) Dwelling the driving member 356 at the end of its advancing action for about 8–10 seconds. (FIG. 28)
7) Activating the air cylinder 350 to retract the driving member 356 engaged with the adaptor 302 to pull the adaptor 302 with the empty applicator 309 (as shown in FIG. 30) from the in vitro receptacle 106, leaving the deployed tampon 305 in the in vitro receptacle 106 with the removal string 307 attached to the tampon 305 and extending out from the in vitro receptacle 106.
8) Inserting the pin plug 370 (as shown in FIG. 31) into the in vitro receptacle 106 in place of the removed adaptor 302; but previously placing the removal string 307 along the grove of the pin plug 370, taking care not to move the tampon while handling the string 307.
9) Photographing the position of the tampon with respect to a low-placement positioning zone 400 inside the in vitro receptacle 106.

Figure 35:
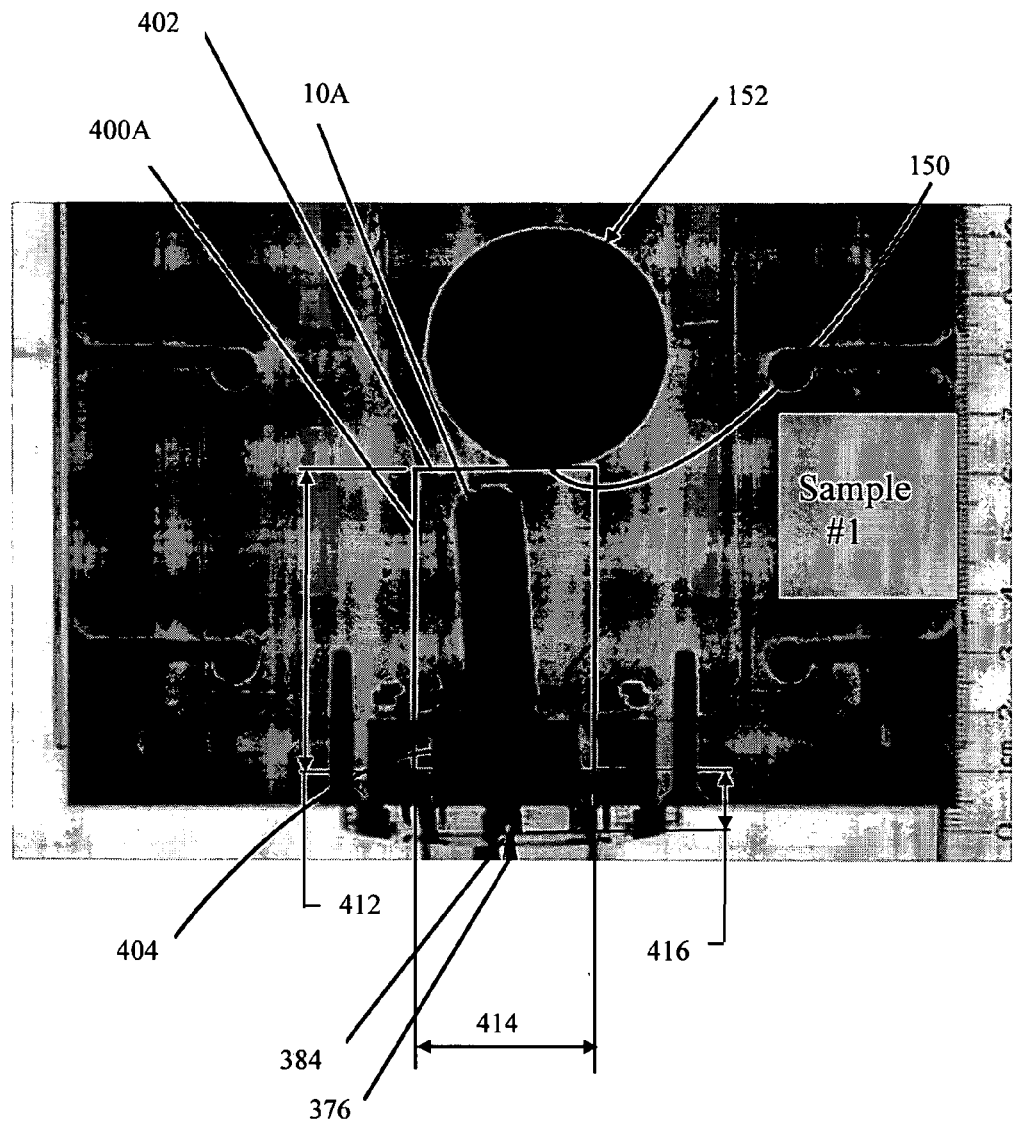
FIG. 35 is an exemplary photograph of a tampon disposed within the boundaries of the most preferred dimensions of the tampon-positioning zone of the present invention.

FIG. 35 is an exemplary photograph of a tampon 10A disposed within the boundaries of the most preferred low-placement positioning zone 400A having the posterior boundary 402 adjacent the deflecting area 150 of the column 152 and the anterior boundary 404 at the anterior depth 416 of about 10 mm (measured from the tip 384 of the pin 376). The length 412 of the low-placement positioning zone 400A is about 49 mm and the width 414 of about 30 mm.

Figure 36:
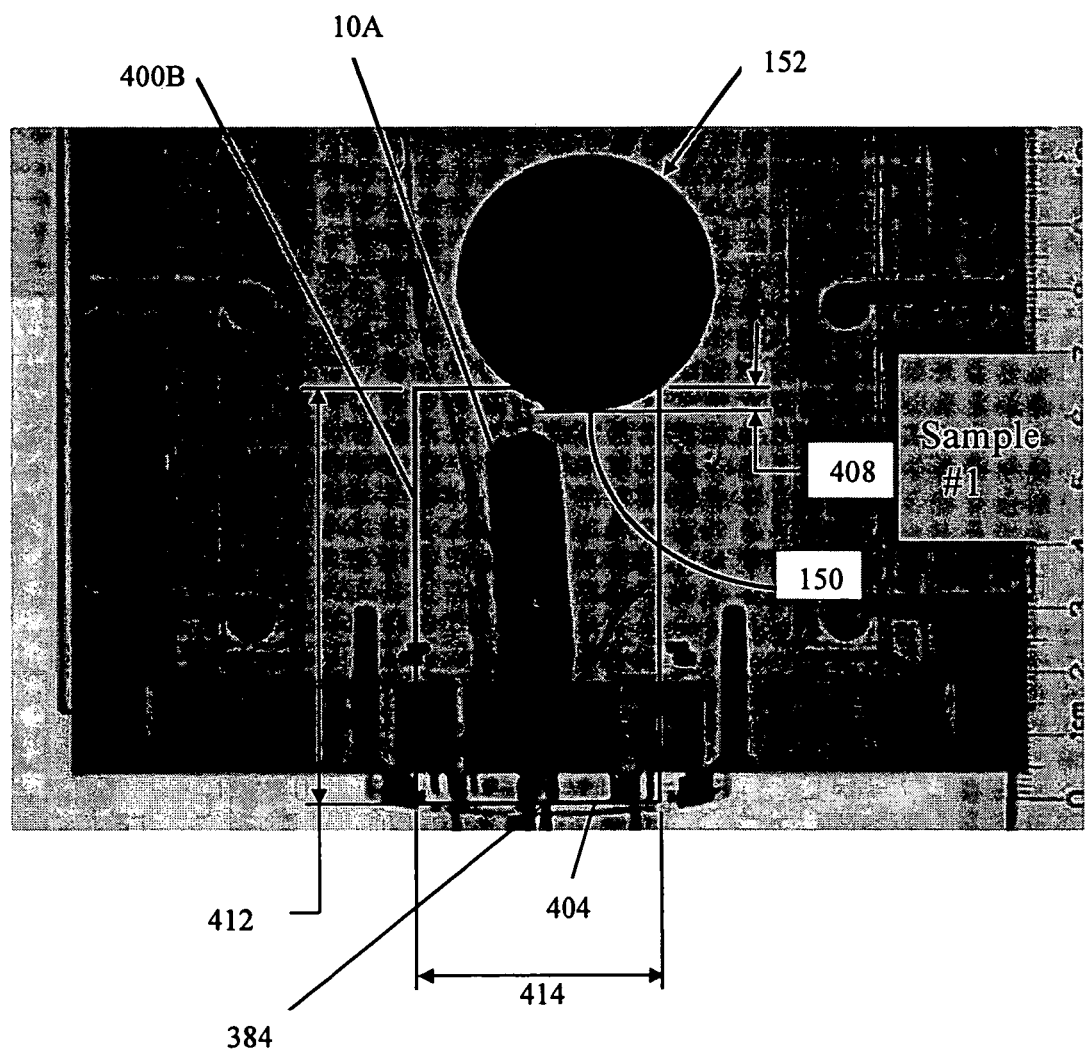
FIG. 36 is an exemplary photograph of a tampon disposed within the boundaries of the least preferred dimensions of the tampon-positioning zone of the present invention.

FIG. 36 is an exemplary photograph of tampon 10A disposed within the boundaries of the least preferred low-placement positioning zone 400B of having the posterior boundary at a posterior depth 408 of about 3 mm and the anterior boundary 404 at zero mm from the tip 384.

Figure 37:
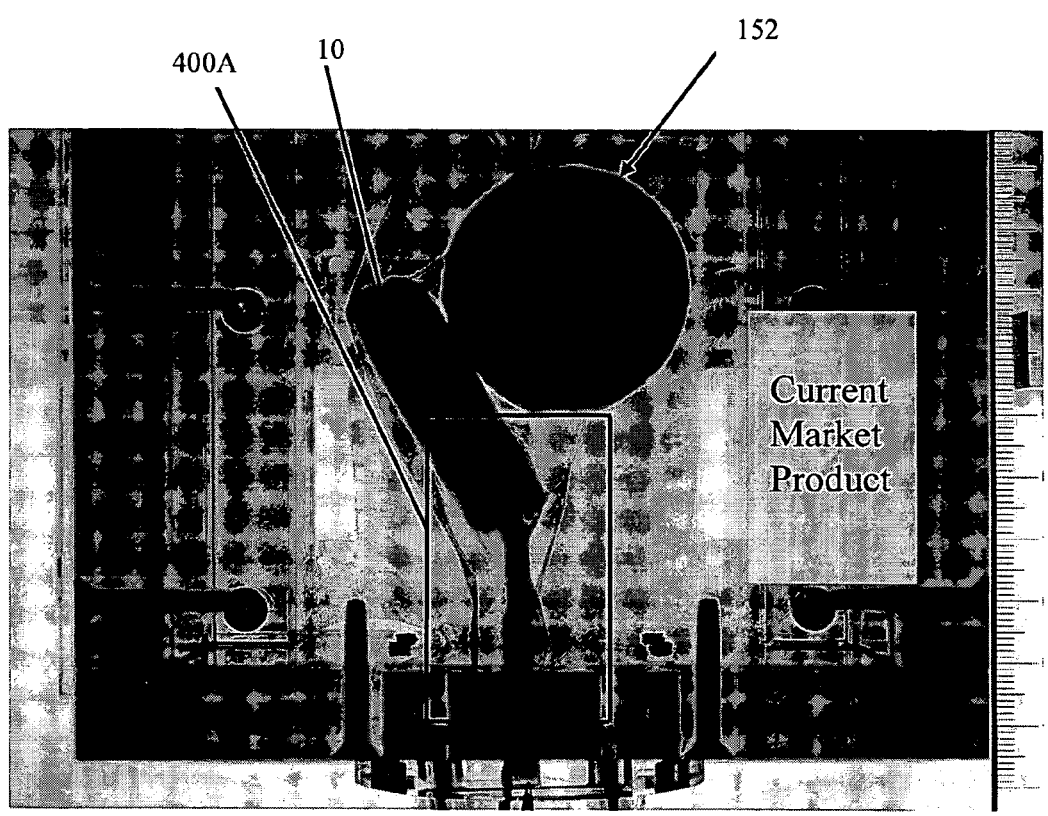
FIG. 37 is an exemplary photograph of a tampon disposed partially outside the boundaries of the most preferred dimensions of the tampon-positioning zone of the present invention.

FIG. 37 is an exemplary photograph of tampon 10 being partially disposed outside the boundaries of the low-placement-positioning zone 400A of the present invention.

All documents cited in the Detailed Description of the Invention are incorporated, in relevant part, herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for in vitro testing of tampon-and-applicator systems, comprising the steps of:
    (a) pressurizing an in vitro receptacle comprising a sleeve having a tampon- deflecting zone to provide a pressure of about 0.6 psi (4.1 Pascal);
    (b) providing a tampon-and-applicator system comprising an applicator at least partially housing a tampon in a larger tube and a smaller tube for ejecting the tampon from the larger tube, the tampon having a removal string attached thereto;
    (c) inserting the tampon-and-applicator system into an adaptor such that a trailing end of a larger tube of the tampon-and-applicator system is even with a trailing end of the adaptor;

(d) inserting the adaptor with the tampon-and-applicator system into an entry of the in vitro receptacle such that a leading end of the adaptor is brought in contact with a base surface in the entry;

(e) activating a driving mechanism to push the smaller tube to eject the tampon from the tampon-and-applicator system into the in vitro receptacle;

(f) removing the adaptor with the applicator from the entry of the in vitro receptacle leaving the tampon in the in vitro receptacle;

(g) inserting a pin plug into the entry of the in vitro receptacle; and (h) photographing the tampon and a low-placement positioning zone disposed inside the in vitro receptacle, the low-placement positioning zone having a width of about 30 mm and forming an anterior depth of about 10 mm of and a posterior depth of 0 mm.

2. The method of claim 1 wherein the anterior depth is about 5 mm.

3. The method of claim 1 wherein the anterior depth is 0 mm.

4. The method of claim 1 wherein the posterior depth is about 3 mm.

5. The method of claim 1 wherein the width of the low-placement-positioning zone is about 40 mm.

6. A tampon-and-applicator system comprising a tampon, an applicator at least partially housing the tampon and a withdrawal element attached thereto, wherein the tampon-and-applicator system provides for placement of the tampon within the boundaries of the low-placement-positioning zone according to the method of claim 1.

7. The system of claim 6 wherein the anterior depth is about 5 mm.

8. The system of claim 6 wherein the anterior depth is 0 mm.

9. The system of claim 6 wherein the posterior depth is about 3 mm.

10. The system of claim 6 wherein the width of the low-placement-positioning zone is about 40 mm.

* * * * *